United States Patent
Kim et al.

(10) Patent No.: US 10,633,696 B2
(45) Date of Patent: Apr. 28, 2020

(54) METHOD FOR ANALYZING 3' END SEQUENCE OF MESSENGER RNA

(71) Applicants: Seoul National University R&DB Foundation, Seoul (KR); INSTITUTE FOR BASIC SCIENCE, Daejeon (KR)

(72) Inventors: V. Narry Kim, Seoul (KR); Jaechul Lim, Seoul (KR); Hyeshik Chang, Anyang-si (KR)

(73) Assignees: Seoul National University R&DB Foundation, Seoul (KR); INSTITUTE FOR BASIC SCIENCE, Daejeon (KR)

( * ) Notice: Subject to any disclaimer, the term of this patent is extended or adjusted under 35 U.S.C. 154(b) by 241 days.

(21) Appl. No.: 15/656,811

(22) Filed: Jul. 21, 2017

(65) Prior Publication Data

US 2018/0119213 A1    May 3, 2018

(30) Foreign Application Priority Data

Oct. 27, 2016    (KR) .................. 10-2016-0141190

(51) Int. Cl.
*C12Q 1/68*    (2018.01)
*C12Q 1/6855*    (2018.01)
*C12Q 1/6869*    (2018.01)
*C12Q 1/6876*    (2018.01)

(52) U.S. Cl.
CPC ......... *C12Q 1/6855* (2013.01); *C12Q 1/6869* (2013.01); *C12Q 1/6876* (2013.01)

(58) Field of Classification Search
CPC ............... C12Q 1/6855; C12Q 1/6869; C12Q 2525/301; C12Q 2565/519
See application file for complete search history.

(56) References Cited

PUBLICATIONS

Lim et al., "mTAIL-seq reveals dynamic poly(A) tail regulation in oocyte-to-embryo development", Genes & Development, pp. 1-12, Jul. 21, 2016.
Chang et al., "TAIL-seq: Genome-wide Determination of Poly(A) Tail Length and 3' End Modifications", Molecular Cell, vol. 53, pp. 1044-1052, (2014).
Subtelny et al., "Poly(A)-tail profiling reveals an embryonic switch in translational control", Nature, vol. 508, pp. 66-71, with 13 additional pages, (2014).
Hoque et al., "Analysis of alternative cleavage and polyadenylation by 3' region extraction and deep sequencing", Nature Methods, Advanced Online Publication, pp. 1-7, with 2 additional pages, (2012).
Wang et al., "RNA-Seq: a revolutionary tool for transcriptomics", Nature Reviews Genetics, vol. 10, pp. 57-63, (2009).
Anders et al., "HTSeq-a Python framework to work with high-throughput sequencing data", Bioinformatics Advance Access publication, vol. 31, No. 2, pp. 166-169, (2015).
Bastock et al., "*Drosophila* Oogenesis", Current Biology, vol. 18, No. 23, R1082-R1087, (2011).
Zheng et al., "Sizing up the poly(A) tail: insights from deep sequencing", Trends in Biochemical Sciences, vol. xxx, No. xx, pp. 1-3, (2014).
Weill et al, "Translational control by changes in poly(A) tail length: recycling mRNAs", Nature Structural & Molecular Biology,, vol. 19, No. 6, pp. 577-585, (2012).
Meijer et al., "A novel method for poly(A) fractionation reveals a large population of mRNAs with a short poly(A) tail in mammalian cells", Nucleic Acids Research, vol. 35, No. 19, pp. 1-13, (2007).
Li et al. "RSEM:accurate transcript quantification from RNA-Seq data with or without a reference Genome", BMC Bioinformatics, vol. 12, No. 323, pp. 1-16, (2011).
Beilharz et al., "Widespread use of poly(A) tail length control to accentuate expression of the yeast transcriptome", RNA, vol. 13, pp. 982-997, (2007).
Lim, "Transcriptome-wide studies on eukaryotic mRNA tail", School of Biological Sciences The Graduate School Seoul National University, pp. 1-170, (Aug. 2016).

*Primary Examiner* — David C Thomas
(74) *Attorney, Agent, or Firm* — Vorys, Sater, Seymour & Pease LLP; Mih Suhn Koh

(57) ABSTRACT

The present disclosure provides a new protocol for sequencing the 3' end of messenger RNA (mRNA). The present disclosure can be very favorably used in analyzing the repetitive sequences of nucleic acids, which are difficult to analyze by current sequencing methods, especially, homopolymeric sequences (poly[A] sequence) of mRNA. The present disclosure has significantly improved sensitivity to mRNA compared with an existing method, thereby obtaining a lot of genetic information from a small amount of sample. The method of the present disclosure reduces the time and cost for sequencing the 3' end of mRNA and can be applied to various samples, and thus, can be used as a useful tool in the study of RNA synthesis/degradation and protein production in association with all life phenomena, including embryogenesis, cancer, and neurotransmission.

11 Claims, 42 Drawing Sheets
Specification includes a Sequence Listing.

C  Position of the 5' end of read 1 relative to the annotated 3' end

A 3' end uridylation frequency (by TAIL-seq)

| | Gene ontology groups |
|---|---|
| G1 | regionalization<br>wing disc development<br>zinc ion binding<br>regulation of RNA metabolic process |
| G2 | regulation of transcription |
| G3 | gamete generation |
| G4 | - |
| G5 | proteasome complex<br>lipid particle<br>proteolysis<br>oxidative phosphorylation<br>chaperonin-containing T-complex |
| G6 | generation of precursor metabolites and energy |
| G7 | - |
| G8 | ribosome<br>ribonucleoprotein complex<br>structural molecule activity<br>translation |

B Correlation between poly(A) tail length change and TE change upon egg activation (0–1 hr)

SEQUENCE LISTING

<160> NUMBER OF SEQ ID NOS: 22

<210> SEQ ID NO 1
<211> LENGTH: 26
<212> TYPE: RNA
<213> ORGANISM: Artificial Sequence
<220> FEATURE:
<223> OTHER INFORMATION: 5' adaptor

<400> SEQUENCE: 1
guucagaguu cuacaguccg acgauc                                    26

<210> SEQ ID NO 2
<211> LENGTH: 22
<212> TYPE: DNA
<213> ORGANISM: Artificial Sequence
<220> FEATURE:
<223> OTHER INFORMATION: RT-PCR primer

<400> SEQUENCE: 2
gccttggcac ccgagaattc ca                                        22

<210> SEQ ID NO 3
<211> LENGTH: 50
<212> TYPE: DNA
<213> ORGANISM: Artificial Sequence
<220> FEATURE:

<223> OTHER INFORMATION: PCR forward primer

<400> SEQUENCE: 3
aatgatacgg cgaccaccga gatctacacg ttcagagttc tacagtccga          50

<210> SEQ ID NO 4
<211> LENGTH: 63
<212> TYPE: DNA
<213> ORGANISM: Artificial Sequence
<220> FEATURE:
<223> OTHER INFORMATION: PCR reverse primer 1

<400> SEQUENCE: 4
caagcagaag acggcatacg agatcgtgat gtgactggag ttccttggca cccgagaatt    60
cca                                                                 63

<210> SEQ ID NO 5
<211> LENGTH: 63
<212> TYPE: DNA
<213> ORGANISM: Artificial Sequence
<220> FEATURE:
<223> OTHER INFORMATION: PCR reverse primer 2

<400> SEQUENCE: 5
caagcagaag acggcatacg agatacatcg gtgactggag ttccttggca cccgagaatt    60
cca                                                                 63

<210> SEQ ID NO 6
<211> LENGTH: 63
<212> TYPE: DNA
<213> ORGANISM: Artificial Sequence
<220> FEATURE:
<223> OTHER INFORMATION: PCR reverse primer 3

<400> SEQUENCE: 6
caagcagaag acggcatacg agatgcctaa gtgactggag ttccttggca cccgagaatt    60
cca                                                                 63

<210> SEQ ID NO 7
<211> LENGTH: 63
<212> TYPE: DNA
<213> ORGANISM: Artificial Sequence
<220> FEATURE:
<223> OTHER INFORMATION: PCR reverse primer 4

<400> SEQUENCE: 7
caagcagaag acggcatacg agattggtca gtgactggag ttccttggca cccgagaatt    60
cca                                                                 63

<210> SEQ ID NO 8
<211> LENGTH: 63
<212> TYPE: DNA
<213> ORGANISM: Artificial Sequence
<220> FEATURE:
<223> OTHER INFORMATION: PCR reverse primer 5

<400> SEQUENCE: 8
caagcagaag acggcatacg agatcactgt gtgactggag ttccttggca cccgagaatt    60
cca                                                                 63

<210> SEQ ID NO 9
<211> LENGTH: 63

```
<212> TYPE: DNA
<213> ORGANISM: Artificial Sequence
<220> FEATURE:
<223> OTHER INFORMATION: PCR reverse primer 6

<400> SEQUENCE: 9
caagcagaag acggcatacg agatattggc gtgactggag ttccttggca cccgagaatt      60
cca                                                                    63

<210> SEQ ID NO 10
<211> LENGTH: 63
<212> TYPE: DNA
<213> ORGANISM: Artificial Sequence
<220> FEATURE:
<223> OTHER INFORMATION: PCR reverse primer 7

<400> SEQUENCE: 10
caagcagaag acggcatacg agatgatctg gtgactggag ttccttggca cccgagaatt      60
cca                                                                    63

<210> SEQ ID NO 11
<211> LENGTH: 63
<212> TYPE: DNA
<213> ORGANISM: Artificial Sequence
<220> FEATURE:
<223> OTHER INFORMATION: PCR reverse primer 8

<400> SEQUENCE: 11
caagcagaag acggcatacg agattcaagt gtgactggag ttccttggca cccgagaatt      60
cca                                                                    63

<210> SEQ ID NO 12
<211> LENGTH: 63
<212> TYPE: DNA
<213> ORGANISM: Artificial Sequence
<220> FEATURE:
<223> OTHER INFORMATION: PCR reverse primer 9

<400> SEQUENCE: 12
caagcagaag acggcatacg agattacaag gtgactggag ttccttggca cccgagaatt      60
cca                                                                    63

<210> SEQ ID NO 13
<211> LENGTH: 80
<212> TYPE: DNA
<213> ORGANISM: Artificial Sequence
<220> FEATURE:
<223> OTHER INFORMATION: Spike-in 0
<220> FEATURE:
<221> NAME/KEY: misc_feature
<222> LOCATION: (25)...(47)
<223> OTHER INFORMATION: a, c, g, or t

<400> SEQUENCE: 13
tcagagttct acagtccgac gatcnnnnnn nnnnnnnnnn nnnnnnnctg acgagctact      60
gttggaattc tcgggtgcca                                                  80

<210> SEQ ID NO 14
<211> LENGTH: 80
<212> TYPE: DNA
<213> ORGANISM: Artificial Sequence
<220> FEATURE:
<223> OTHER INFORMATION: Spike-in 8
<220> FEATURE:
```

<221> NAME/KEY: misc_feature
<222> LOCATION: (25)...(38)
<223> OTHER INFORMATION: a, c, g, or t

<400> SEQUENCE: 14
tcagagttct acagtccgac gatcnnnnnn nnnnnnnnba aaaaaaactg acgagctact    60
gttggaattc tcgggtgcca                                                80

<210> SEQ ID NO 15
<211> LENGTH: 88
<212> TYPE: DNA
<213> ORGANISM: Artificial Sequence
<220> FEATURE:
<223> OTHER INFORMATION: Spike-in 16
<220> FEATURE:
<221> NAME/KEY: misc_feature
<222> LOCATION: (25)...(38)
<223> OTHER INFORMATION: a, c, g, or t

<400> SEQUENCE: 15
tcagagttct acagtccgac gatcnnnnnn nnnnnnnnba aaaaaaaaaa aaaaactgac    60
gagctactgt tggaattctc gggtgcca                                       88

<210> SEQ ID NO 16
<211> LENGTH: 104
<212> TYPE: DNA
<213> ORGANISM: Artificial Sequence
<220> FEATURE:
<223> OTHER INFORMATION: Spike-in 32
<220> FEATURE:
<221> NAME/KEY: misc_feature
<222> LOCATION: (25)...(38)
<223> OTHER INFORMATION: a, c, g, or t

<400> SEQUENCE: 16
tcagagttct acagtccgac gatcnnnnnn nnnnnnnnba aaaaaaaaaa aaaaaaaaaa    60
aaaaaaaaaa actgacgagc tactgttgga attctcgggt gcca                    104

<210> SEQ ID NO 17
<211> LENGTH: 136
<212> TYPE: DNA
<213> ORGANISM: Artificial Sequence
<220> FEATURE:
<223> OTHER INFORMATION: Spike-in 64
<220> FEATURE:
<221> NAME/KEY: misc_feature
<222> LOCATION: (25)...(38)
<223> OTHER INFORMATION: a, c, g, or t

<400> SEQUENCE: 17
tcagagttct acagtccgac gatcnnnnnn nnnnnnnnba aaaaaaaaaa aaaaaaaaaa    60
aaaaaaaaaa aaaaaaaaaa aaaaaaaaaa aaaaaaaaaa aaactgacga gctactgttg   120
gaattctcgg gtgcca                                                   136

<210> SEQ ID NO 18
<211> LENGTH: 191
<212> TYPE: DNA
<213> ORGANISM: Artificial Sequence
<220> FEATURE:
<223> OTHER INFORMATION: Spike-in 118
<220> FEATURE:
<221> NAME/KEY: misc_feature
<222> LOCATION: (25)...(38)
<223> OTHER INFORMATION: a,c, g, or t

<400> SEQUENCE: 18

```
tcagagttct acagtccgac gatcnnnnnn nnnnnnnnba aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaact gacgagctac tgttggaatt    180
ctcgggtgcc a                                                         191
```

```
<210> SEQ ID NO 19
<211> LENGTH: 201
<212> TYPE: DNA
<213> ORGANISM: Artificial Sequence
<220> FEATURE:
<223> OTHER INFORMATION: Spike-in 128
<220> FEATURE:
<221> NAME/KEY: misc_feature
<222> LOCATION: (25)...(38)
<223> OTHER INFORMATION: a,c, g, or t

<400> SEQUENCE: 19
```

```
tcagagttct acagtccgac gatcnnnnnn nnnnnnnnba aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaact gacgagctac    180
tgttggaatt ctcgggtgcc a                                              201
```

```
<210> SEQ ID NO 20
<211> LENGTH: 72
<212> TYPE: DNA
<213> ORGANISM: Artificial Sequence
<220> FEATURE:
<223> OTHER INFORMATION: 3' hairpin adaptor 1
<220> FEATURE:
<221> NAME/KEY: misc_feature
<222> LOCATION: (9)...(20)
<223> OTHER INFORMATION: a,c, g, or t
<220> FEATURE:
<221> NAME/KEY: misc_feature
<222> LOCATION: (1)
<223> OTHER INFORMATION: 5Phos(5' phosphorylation)
<220> FEATURE:
<221> NAME/KEY: misc_feature
<222> LOCATION: (42)...(43)
<223> OTHER INFORMATION: iSpC3//idSp//idSp//iBiodT//iBiodT are present
      between the nucleotides
<220> FEATURE:
<221> NAME/KEY: misc_feature
<222> LOCATION: (56)...(57)
<223> OTHER INFORMATION: iSp18 is present between the nucleotides
<220> FEATURE:
<221> NAME/KEY: misc_feature
<222> LOCATION: (72)
<223> OTHER INFORMATION: 3InvdT(3' inverted deoxythymidine)

<400> SEQUENCE: 20
```

```
ctgacatgnn nnnnnnnnnn tggaattctc gggtgccaag gcggcacccg agaattcatg      60
tcagtttttt tt                                                         72
```

```
<210> SEQ ID NO 21
<211> LENGTH: 72
<212> TYPE: DNA
<213> ORGANISM: Artificial Sequence
<220> FEATURE:
<223> OTHER INFORMATION: 3' hairpin adaptor 2
<220> FEATURE:
<221> NAME/KEY: misc_feature
<222> LOCATION: (9)...(20)
<223> OTHER INFORMATION: a,c, g, or t
<220> FEATURE:
<221> NAME/KEY: misc_feature
```

```
<222> LOCATION: (1)
<223> OTHER INFORMATION: 5Phos(5' phosphorylation)
<220> FEATURE:
<221> NAME/KEY: misc_feature
<222> LOCATION: (42)...(43)
<223> OTHER INFORMATION: iSpC3//idSp//idSp//iBiodT//iBiodT are present
      between the nucleotides
<220> FEATURE:
<221> NAME/KEY: misc_feature
<222> LOCATION: (56)...(57)
<223> OTHER INFORMATION: iSp18 is present between the nucleotides
<220> FEATURE:
<221> NAME/KEY: misc_feature
<222> LOCATION: (71)
<223> OTHER INFORMATION: 3InvdT(3' inverted deoxythymidine)

<400> SEQUENCE: 21
ctgacatgnn nnnnnnnnnn tggaattctc gggtgccaag gcggcacccg agaattcatg     60
tcagattttt tt                                                        72

<210> SEQ ID NO 22
<211> LENGTH: 72
<212> TYPE: DNA
<213> ORGANISM: Artificial Sequence
<220> FEATURE:
<223> OTHER INFORMATION: 3' hairpin adaptor 3
<220> FEATURE:
<221> NAME/KEY: misc_feature
<222> LOCATION: (9)...(20)
<223> OTHER INFORMATION: a,c, g, or t
<220> FEATURE:
<221> NAME/KEY: misc_feature
<222> LOCATION: (1)
<223> OTHER INFORMATION: 5Phos(5' phosphorylation)
<220> FEATURE:
<221> NAME/KEY: misc_feature
<222> LOCATION: (42)...(43)
<223> OTHER INFORMATION: iSpC3//idSp//idSp//iBiodT//iBiodT are present
      between the nucleotides
<220> FEATURE:
<221> NAME/KEY: misc_feature
<222> LOCATION: (56)...(57)
<223> OTHER INFORMATION: iSp18 is present between the nucleotides
<220> FEATURE:
<221> NAME/KEY: misc_feature
<222> LOCATION: (72)
<223> OTHER INFORMATION: 3InvdT(3' inverted deoxythymidine)

<400> SEQUENCE: 22
ctgacatgnn nnnnnnnnn tggaattctc gggtgccaag gcggcacccg agaattcatg      60
tcagaatttt tt                                                        72
```

METHOD FOR ANALYZING 3' END SEQUENCE OF MESSENGER RNA

CROSS-REFERENCE TO RELATED APPLICATIONS

This application claims the benefit and priority of Korean Patent Application No. 10-2016-0141190, filed Oct. 27, 2016. The entire disclosure of the above application is incorporated herein by reference.

SEQUENCE LISTING

The Sequence Listing submitted in text format (.txt) filed on Nov. 15, 2019, named "SequenceListing.txt", created on Nov. 15, 2019, 8.06 KB), is incorporated herein by reference.

TECHNICAL FIELD

The present disclosure relates to a method for analyzing 3' end sequences of messenger RNA.

BACKGROUND ART

The poly(A) tail existing at the 3' end of messenger RNA (mRNA) is an important factor in determining the fate of mRNA. The mRNA produced in the nucleus is transported to the cytoplasm after elongation of the poly(A) tail, and the poly(A) tail blocks the degradation of RNA in the cytoplasm and promotes translation. However, when the poly(A) tail of mRNA get shortened, translation does not occur and RNA degradation is promoted. Therefore, the accurate measurement of the poly(A) tail length provides important information in the study of the stability of mRNA and the production of protein.

The poly(A) tail length in oocytes and early embryos of various animal models has been known to have a crucial influence on protein synthesis. However, these results have been demonstrated only for particular individual genes, and have not been thoroughly studied at the global gene level due to experimental limitations.

Throughout the entire specification, many papers and patent documents are referenced and their citations are represented. The disclosures of cited papers and patent documents are entirely incorporated by reference into the present specification, and the level of the technical field within which the present disclosure falls and details of the present disclosure are explained more clearly.

SUMMARY

Technical Problem

The present inventors have researched and endeavored to develop a method capable of promptly and accurately analyzing the 3' end sequences of mRNA, which plays an important role in genetic regulation. The inventors have established a method for analyzing the 3' end sequences of mRNA by ligating a 3' hairpin adaptor to the 3' end of mRNA, randomly digesting the mRNA body, ligating a 5' adaptor to the 5' end, and performing sequencing. As a result, the inventors have efficiently analyzed the 3' end sequences of mRNA from a small amount of sample.

Therefore, in an embodiment, the present disclosure provides a 3' hairpin adaptor for analyzing the 3' end sequences of mRNA.

In another embodiment, the present disclosure provides a method for analyzing the 3' end sequences of mRNA.

Other purposes and advantages of the present disclosure will be clarified by the following detailed description of the invention, claims, and drawings.

Technical Solution

In accordance with an embodiment of the present disclosure, there is provided a 3' hairpin adaptor containing a 5' arm and a 3' arm for analyzing the 3' end sequences of mRNA, the 3' hairpin adaptor including:

i) a first stem region including 6-12 base pairs, wherein the base pairs are base pairs including nucleotides of a 5' arm, self-hybridized with nucleotides of a 3' arm;

ii) a first loop region including a 5' arm including 10-20 unpaired nucleotides, wherein a 3' arm corresponding to the 5' arm includes nucleotides unpaired with the 5' arm or is a spacer;

iii) a second stem region including 10-22 base pairs, wherein the base pairs are base pairs including nucleotides of a 5' arm, self-hybridized with nucleotides of a 3' arm, and include at least one biotinylated nucleotide at a 5' end of the 3' arm, hybridized with a 3' end of the 5' arm, in the stem region;

iv) a second loop region including an endonuclease recognition site; and v) a poly(A) tail binding region linked to the 3' arm of the first stem region in an overhang manner. According to an embodiment of the present disclosure, the 5' nucleotide end of the 5' arm of the first stem region constituting the 3' hairpin adaptor is phosphorylated.

According to another embodiment of the present disclosure, the 3' nucleotide end of the 3' arm constituting the 3' hairpin adaptor further includes 3' inverted deoxythymidine (3InvdT). The 3InvdT is an example of an inactivated nucleotide sequence used to inhibit the digestion of the 3' end by exonuclease, the ligation of a nucleotide sequence by ligase, or the synthesis of a nucleotide sequence by polymerase, and is not necessarily limited to 3InvdT.

According to still another embodiment of the present disclosure, in the 3' hairpin adaptor of the present disclosure, the biotinylated nucleotide in the second stem region iii) may be a biotinylated thymine, but is not limited thereto.

In addition, according to another embodiment of the present disclosure, for an endonuclease recognition site included in the second loop region, any recognition site of endonuclease may be used regardless of the kind thereof as long as it is a recognition site of endonuclease recognizing and digesting an inner portion of a nucleotide sequence, and for example, recognition sites of EcoRI (recognizing 5'-GAATTC-3') and BamHI (recognizing 5'-GGATCC-3') may correspond thereto. More specifically, the endonuclease recognition site is internal 1',2'-dideoxyribose)/idsP (idSP), and a recognition site by apurinic/apyrimidinic endonuclease 1 (APE1) may be used, but is not limited thereto.

According to still another embodiment of the present disclosure, when the 3' arm of the first loop region ii) is a spacer, the spacer may be specifically an 18-atom hexaethyleneglycol spacer, but is not limited thereto.

Furthermore, according to another embodiment, the second loop region iv) of the 3' hairpin adaptor of the present disclosure may include a C3 spacer, but is not limited thereto.

According to an embodiment, the poly(A) tail binding region v) is composed of 6-12 consecutive thymine nucleotides, which is linked to the 3' arm of the first stem region in an overhang form, and therefore, the thymine nucleotides may form a double-stranded structure by binding complementary to the poly(A) tail of the mRNA. Here, in cases where the 5' end in the consecutive-thymine nucleotides is substituted with 1-2 adenine nucleotides, mRNA having an uridylated 3' end can be easily detected.

For example, the poly(A) tail binding region of the 3' hairpin adaptor of the present disclosure is composed of an overhang nucleotide sequence of consecutive thymine nucleotides, such as 5'-TTTTTTTT-3', 5'-ATTTTTTT-3', or 5'-AATTTTTT-3', and the nucleotide sequence of 5'-TTTTTTTT-3', 5'-ATTTTTTT-3', or 5'-AATTTTTT-3' complementarily binds to the 3' end of the poly(A) tail of the mRNA having a nucleotide sequence 5'-AAAAAAAA-3', 5'-AAAAAAAU-3', or 5'-AAAAAAUU-3' to allow the detection of uridylated mRNA.

In addition, according to a particular embodiment of the present disclosure, the 3' hairpin adaptor of the present disclosure may include a structure of 5'-/5Phos/CTGACAT-GNNNNNNNNNNNNNTGGAATTCTCGGGTGC-CAAGGC/iSpC3//id Sp//idSp//iBiodT//iBiodT/GGCAC-CCGAGAATT/iSp18/CATGTCAGTTTTTTTT/3Invd T/-3' (SEQ ID NO: 20), a structure of 5'-/5Phos/CTGACAT-GNNNNNNNNNNNNNTGGAATTCTCGGGTGC-CAAGGC/iSpC3//id Sp//idSp//iBiodT//iBiodT/GGCAC-CCGAGAATT/iSp18/CATGTCAGATTTTTTT/3Invd T/-3' (SEQ ID NO: 21), or a structure of 5'-/5Phos/CTGACAT-GNNNNNNNNNNNNNTGGAATTCTCGGGTGC-CAAGGC/iSpC3//id Sp//idSp//iBiodT//iBiodT/GGCAC-CCGAGAATT/iSp18/CATGTCAGAATTTTTT/3 Invd T/-3' (SEQ ID NO: 22), but is not limited thereto.

In accordance with another aspect of the present disclosure, there is provided a method for analyzing the 3' end sequences of mRNA (mRNA), the method including:

(a) ligating a 3' hairpin adaptor to a 3' end of mRNA;

(b) partially digesting the 3' hairpin adaptor-ligated mRNA;

(c) obtaining the digested mRNA to perform 5' end phosphorylation and endonucleolytic cleavage reactions on the digested mRNA;

(d) purifying the 300-750 nt mRNA from the product in step (C) and ligating a 5' adaptor to a 5' end thereof;

(e) reverse-transcribing and amplifying mRNA, which is the product in step (d); and (f) sequencing the amplified product.

The present inventors have researched and endeavored to develop a method capable of promptly and accurately sequencing the 3' end of mRNA, which plays an important role in genetic regulation. The inventors have established a method for analyzing the 3' end sequences of mRNA by ligating a 3' hairpin adaptor to the 3' end of mRNA, randomly digesting the mRNA body, ligating a 5' adaptor to the 5' end, and performing sequencing. As a result, the inventors have efficiently analyzed the 3' end sequence of mRNA from a small amount of sample. The method of the present disclosure is termed "mTAIL-seq".

It has been known that mRNA in a cell has a poly(A) tail at the 3' end thereof and the length of the poly(A) tail has an influence on RNA stability and translational efficiency into proteins. Therefore, the measurement of the poly(A) tail length provides important information in studying RNA degradation and the regulation of protein production.

The present inventors previously developed TAIL-seq, capable of analyzing 3' terminal nucleotide sequences of RNA at the global level (Chang H, Lim J, Ha M, Kim V N. 2014. TAIL-seq: genome-wide determination of poly(A) tail length and 3' end modifications. Mol Cell 53: 1044-41052.), but it has been infeasible to apply this method to a small amount of sample, such as oocytes or early embryos, since it is difficult to obtain a sufficient RNA. Therefore, the present inventors have newly developed mTAIL-seq (mRNA TAIL-seq) with significantly improved sensitivity to mRNA by improving TAIL-seq. mTAIL-seq is an efficient method capable of obtaining a lot of information from a small amount of sample. According to the present disclosure, through application of this method, the tail lengths of thousands of mRNAs could be accurately measured and their changes upon developmental stages could be observed in immature oocytes, mature oocytes, and early embryos of *Drosophila*. In addition, the inventors revealed the correlation between poly(A) tail length and translational efficiency. Through this, the present inventors validated that the changes in the poly(A) tail length through post-transcriptional regulation play an important role in the regulation of protein production in early embryos.

Meanwhile, the present inventors first found that most mRNA species were polyadenylated during the maturation of *Drosophila* oocytes, and revealed that further modulation at the gene-level occurs upon egg activation. In addition, it was shown that these changes of poly(A) tail are the result from post-transcriptional regulation via the action of cytoplasmic non-canonical poly(A) polymerase, Wispy, independently of transcription.

In addition, to investigate an effect of poly(A) tail regulation on protein synthesis, the inventors compared poly(A) tail length in each developmental stage with translational efficiency which was measured by ribosome profiling. As a result, genes with elongated poly(A) tail showed increased translational efficiency during egg activation, and vice versa, suggesting that global changes in poly(A) tail are highly correlated to translational efficiency at this stage. These are meaningful results showing that the proteins necessary for the early embryogenesis can be selectively and efficiently produced by regulating the length of the poly(A) tail.

The present disclosure will be described in detail by steps as follows:

Step (a): Ligating the 3' Hairpin Adaptor to the 3' End of mRNA

According to the present disclosure, total RNA was extracted from biological samples.

The biological sample used for obtaining the RNA to be analyzed in the present disclosure includes various biological samples, and examples thereof include cells, tissues, viruses, bacteria, blood, lymph, bone marrow fluid, saliva, milk, urine, feces, ocular fluid, semen, brain extract, spinal fluid, joint fluid, thymus fluid, ascites, amniotic fluid, and cell tissue fluid, but are not limited thereto.

According to an embodiment of the present disclosure, the 3' hairpin adaptor is ligated to the 3' end of the RNA to be analyzed, that is, mRNA.

The 3' hairpin adaptor used in the method of the present disclosure is the 3' hairpin adaptor for sequencing the 3' end of the mRNA, and overlapping contents therebetween will be omitted to avoid excessive complexity of the present specification.

According to a particular embodiment of the present disclosure, the 3' hairpin adaptor includes 5'-/5Phos(5' phosphorylation)/CTGACATGNNNNNNNNNNNNNTGGAAT-TCTCGGGTGCCAAGGC/iSpC3(internal C3 phosphoramidite)//idSp(internal 1',2'-dideoxyribose)//idSp//iBiodT (internal biotinylated deoxythymidine)//iBiodT/GGCACCCGAGAATT/iSp18(internal 18-atomhexaethyleneglycol spacer)/CATGTCA-GTTTTTTTT/3InvdT(3' inverted deoxythymidine)/-3'

(SEQ ID NO: 20), 5'-/5Phos/CTGACAT-GNNNNNNNNNNNNNTGGAATTCTCGGG TGC-CAAGGC/iSpC3//idSp//idSp//iBiodT//iBiodT/GGCAC-CCGAGAATT/iSp18/CATG TCAGATTTTTTT/3InvdT/-3' (SEQ ID NO: 21), or 5'-/5Phos/CTGACAT-GNNNNNNNNNNNNNTGGAATTCTCGGG TGC-CAAGGC/iSpC3//idSp//idSp//iBiodT//iBiodT/GGCAC-CCGAGAATT/iSp18/CATG TCAGAATTTTTT/3InvdT/-3' (SEQ ID NO: 22). The 3' hairpin adaptor used in the present disclosure can be described referring to FIG. 1a.

According to an embodiment of the present disclosure, the 3' hairpin adaptor further includes biotins as affinity binding sites.

Herein, the term "ligation" refers to connecting of the 3' end of mRNA and the 5' end of the 3' hairpin adaptor through a covalent bond or a linker.

Step (b): Partially Digesting mRNA

Then, mRNA is partially digested using RNase. A specific example of RNase used to digest mRNA is RNase T1.

As used herein, the term "digestion" refers to fragmentation of the endonucleolytic or exonucleolytic site of nucleotides by enzymatic treatment.

The product in step (b) is digested into at least two fragments.

Step (c): Performing 5' End Phosphorylation and Endonucleolytic Cleavage on mRNA Then, the cleaved and 3' hairpin adaptor-ligated mRNA is purified (e.g, pull-down) using the affinity binding site of the 3' hairpin adaptor. For example, the cleaved and 3' hairpin adaptor-ligated mRNA can be isolated using streptavidin when the affinity binding site is biotin.

According to an embodiment of the present disclosure, the 5' end of the isolated mRNA is phosphorylated through a polynucleotide kinase (PNK) reaction and endonucleolytically cleaved through an APE1 reaction.

The endonucleolytic cleavage in step (c) is the cleavage of an apurinic-apyrimidinic site (AP) of the 3' hairpin adaptor, and is different from the digestion in step (b).

Step (d): mRNA Purification and 5' Adaptor Ligation

According to an embodiment of the present disclosure, the mRNA undergoing 5' end phosphorylation and endonucleolytic cleavage is purified to a predetermined size (e.g., 300-750 nt) range using a conventional size fraction method (e.g., gel fractionation), and then a 5' adaptor is ligated to the 5' end thereof.

According to an embodiment of the present disclosure, the 5' adaptor includes nucleotides represented by SEQ ID NO: 1.

Step (e): mRNA Amplification

The 3' hairpin adaptor- and 5' hairpin adaptor-ligated mRNA obtained from step (d) is subjected to reverse transcription, thereby preparing cDNA.

According to an embodiment of the present disclosure, the reverse transcription may be performed by reverse transcription PCT (RT-PCR). The nucleotide sequence of SEQ ID NO: 2 may be used for a primer used for the RT-PCR.

PCR is performed on the above prepared cDNA, thereby obtaining amplified products.

According to an embodiment of the present disclosure, with respect to primers used in PCR, a primer pair composed of a forward primer including SEQ ID NO: 3 and a reverse primer selected from primers including SEQ ID NO: 4 to SEQ ID NO: 12 may be used.

Step (f): Sequencing Amplified Product

The amplified product obtained in step (e) is sequenced.

In the present disclosure, sequence signals through the sequencing may be obtained by various known methods in the art using bases A, T, C, and G in which different labels are conjugated to the four types of bases, and the labels are specifically fluorescent labels.

A sequence signal for the mRNA 3' end sequence may be obtained by, for example, the Sanger method, see: Sanger F, et al., *J. Mol. Biol.* 94 (3):441-8(1975); Sanger F, et al., *Proc. Natl. Acad. Sci. U.S.A.* 74 (12):5463-7(1977)); the 454 method (see: Ronaghi et al. *Science* 281(5375):363(1998)); or the Illumina method (see: Meyer M., et al., Illumina Sequencing Library Preparation for Highly Multiplexed Target Capture and Sequencing. Cold Springs Harbor Protocols(2010), WO 98/44151; WO 98/44152).

Sequencing through the Illumina method is carried out such that a mononucleotide synthesis reaction is conducted using the four types of fluorescence-labeled nucleotides, and sequence signals generated therefrom are used to determine a sequence.

According to a general Illumina method, a nucleotide sequence is determined according to fluorescence signals for respective nucleotides occurring through the mononucleotide synthesis reaction. As the mononucleotide synthesis reaction proceeds, the already bound fluorescence-labeled nucleotide comes off of a template. In cases where a nucleotide is repeated, such repetitive nucleotides tend not to be readily removed from the template. Therefore, when there are repetitive nucleotides, fluorescence signals for the repetitive nucleotides are strongly accumulated, and thus a next coming nucleotide may be erroneously analyzed as the repetitive nucleotide. For example, as the mononucleotide synthesis reaction proceeds, the already bound fluorescence-labeled nucleotide comes off of the template, and here, fluorescence-labeled nucleotides corresponding to a "T" nucleotide exhibit the characteristics of not coming off of the template as easily as other fluorescence-labeled nucleotides, and this characteristics is shown strongly when the "T" nucleotide continues (e.g., TTT). This characteristic is problematic in that the T fluorescence signal is strongly generated when the T nucleotide continues, and thus, even when a sequence other than the T nucleotide is present as the next occurring nucleotide this next nucleotide is erroneously analyzed as a T nucleotide.

The method of the present disclosure overcomes the above-described sequencing error, thereby accurately analyzing the number of repetitive nucleotides (e.g., T sequence) and the next occurring nucleotide other than a repetitive nucleotide (e.g., T sequence).

When the present disclosure is applied to the analysis of the poly(A) sequence of mRNA, a normalized T signal can be obtained as follows:

(a) calculating a normalized factor for a channel measuring a signal of each nucleotide using equation 1 below $$N_b = \frac{\sum_{j=R_a}^{R_{a'}} S_{j,b}}{(R_{a'} - R_a + 1)} \qquad \text{Equation 1}$$

(in equation 1, $N_b$ represents the normalization factor for channel b in the current spot; $R_a$ represents the first position of degenerate bases region; $R_{a'}$ represents the last position of the degenerate bases region; and $S_{j,b}$ represents the original signal intensity from the n-th base of channel b);

(b) calculating the normalized signal intensity for a 3' end site to be analyzed using equation 2 below $$F_{n,b} = \frac{S_{n,b} + \lambda}{N_b + \lambda} \qquad \text{Equation 2}$$

(in equation 2, $F_{n,b}$ represents a normalized signal intensity for the n-th nucleotide sequence of channel b; and $\lambda$ represents a pseudo count for avoiding zero division); and (c) calculating a normalized T signal using equation 3 below, $$T_n = \log_2 \frac{F_{n,T} + \lambda}{\lambda + \sum_{b=A,C,G} F_{n,b}} \qquad \text{Equation 3}$$

(in equation 3, Tn represents a relative T signal for n-th nucleotide).

The normalized T signal thus obtained is applied to an accurate algorithm, so that sequences of the mRNA 3' end site, especially poly(A) sequence, can be determined.

According to an embodiment of the present disclosure, the normalized T signal is applied to each sequencing cycle to perform sequencing using a Gaussian mixture hidden Markov model. Specifically, the Gaussian mixture hidden Markov model is a model trained to detect poly(A), using a normalized signal obtained from poly(A) spike-in, and a Baum-Welch algorithm may be used in the training. Sequencing using the Gaussian mixture hidden Markov model may be conducted using a Viterbi algorithm.

In the present disclosure, sequencing is performed in an Illumina manner, and the number of nucleotides in mRNA to be sequenced is 30-70 nt (lead 1) at the 5' end to which the 5' adaptor is ligated, and 232-272 nt (lead 2) at the 3' end to which the 3' hairpin adaptor is ligated (see examples).

According to a particular embodiment, the number of nucleotides in mRNA to be sequenced by an Illumina method is 51 nt (lead 1) at the 5' end to which the 5' adaptor is ligated, and 251 nt (lead 2) at the 3' end, to which the 3' hairpin adaptor is ligated.

The 5' end sequence is used to identify the type of mRNA to be analyzed, and the 3' end sequence is used to analyze the length of the poly (A) sequence. For example, the 5' end sequence is used to map the genome of mRNA to be analyzed, and the 3' end sequence is used to analyze the length of the poly (A) sequence.

The method of the present disclosure may be used in the determination and analysis of the length of the poly(A) sequence.

Advantageous Effects

The features and advantages of the present disclosure are summarized as follows:

(a) The present disclosure provides a new protocol for sequencing the 3' end of mRNA.

(b) The present disclosure can be very favorably used in analyzing the repetitive sequences of nucleic acid molecules, which are difficult to analyze by current sequencing methods, especially, homopolymeric sequences ((poly(A) sequence) of mRNA.

(c) The present disclosure has significantly improved sensitivity to mRNA compared with an existing method, thereby obtaining a lot of genetic information from a small amount of a sample.

(d) The method of the present disclosure reduces the time and cost for sequencing the 3' end of mRNA and can be applied to various samples, and thus, can be used as a useful tool in the study of RNA synthesis/degradation and protein production in association with all life phenomena, including embryogenesis, cancer, and neurotransmission.

BRIEF DESCRIPTION OF THE DRAWINGS

FIG. 1a: Schematic of experimental procedures. (left) TAIL-seq, (right) mTAIL-seq. Common steps are shown in black color while red indicates method-specific procedures. Blue bars and black bars represent mRNAs and 3' adaptors, respectively. N (random sequence) and T (thymine) shown in 3' adaptors are abbreviated proportional to the original length. B refers to a biotin.

FIG. 1b: Ligation efficiency test. 5' labeled substrates which have various tails (A10, A10U10, and A50) are ligated with denoted 3' adaptor (mTAIL-seq-1 and mTAIL-seq-2). Blue bar refers to 20 nt heterogeneous sequences (5'-UUUAUUACAGCUCUACCUAG-3'). Black bar represents the 3' adaptor. N (random sequence) and T (thymine) shown in adaptors are abbreviated to the original length. Red arrows indicate the ligated products. Dashed line marks discontinuous lanes from the same gel.

FIG. 1c: TAIL-seq reads are enriched in the 3' part of genes. X-axis shows a relative distance between the 5' end of read 1 and the annotated 3' end.

FIG. 1d: Scatter plots showing the correlation between poly(A) tail lengths measured with four different amounts of input RNA from HeLa. Rp refers to Pearson correlation coefficient.

FIG. 1e: Comparison of poly(A) tail lengths estimated by TAIL-seq and mTAIL-seq. Rp refers to Pearson correlation coefficient.

FIG. 1f: Detection of U-tails by mTAIL-seq. (Top) 3' adaptors used in TAIL-seq and mTAIL-seq are shown in black bars. The nucleotide composition of overhang is denoted in the name (T8, T7A1, and T6A2). Blue bar refers to 3' end of transcript. (Bottom) Poly(A) tail lengths from 8 nt to 231 nt are pooled in equal-width bins in the logarithmic scale (base 2) (x-axis). The left sides of bins (inclusive) are 8, 11, 15, 20, 26, 34, 46, 61, 81, 108, 144, 192 nt. Uridylation frequency (y-axis) indicates the percentage of mono-U and di-U tails within each length range.

FIG. 1g: An example of the analysis procedure for poly (A) length measurement. Shown is a spike-in ($A_{64}$) cluster from cycles corresponding to the 50th to 75th nucleotides from the 3' end. 'Images from sequencer' indicates serial pictures of a cluster taken in each sequencing cycle (red for C, green for T, blue for G; red also reflect A signal due to innate crosstalk between fluorophores). 'Fluorescence signal' is the scaled signal intensity measured from the images. 'Base call' shows the sequence determined by built-in software (Illumina RTA). 'Normalized T signal' indicates the T signal divided by the sum of other signals (A, C, and G), which was then used for machine learning to judge whether or not the cycle is from poly(A) region ('State decoding').

FIG. 2a: Design of the 3' hairpin adaptor. (N) Random sequence.

FIG. 2b: Schematic description of the experimental procedure. (Blue bars) mRNAs; (black bars) 3' adaptors. Random sequence (N) and thymine (T) shown in 3' adaptors are abbreviated proportional to the original length (shown in A). (B) Biotin; (S) streptavidin bead.

FIG. 2c: Accuracy assessment using poly(A) spike-ins. A cumulative graph of poly(A) tail length of chemically synthesized spike-ins (A8, A16, A32, A64, and A118) measured by the TAIL-seq algorithm.

FIG. 2d A box plot showing the read proportion of coding sequences (CDSs) and UTRs in TAIL-seq and mTAIL-seq. For comparison, 12 libraries of TAIL-seq and 13 libraries of mTAIL-seq made from HeLa cells were used. The box indicates the first and third quartiles, and the internal bar refers to the median. Whiskers denote the lowest and highest values within 1.5 times the interquartile range of the first and third quartiles, respectively.

FIG. 2e: A box plot showing the number of detected genes that are normalized by 1 million reads in TAIL-seq and mTAIL-seq. Box and whisker plots are shown as in d.

FIG. 2f: Global distributions of poly(A) tails (8-225 nt) from four different amounts of HeLa RNA.

FIG. 3a: 3' uridylation frequency of mRNAs with short poly(A) tail (5-25 nt) detected by TAIL-seq. Three independent biological replicates from embryos (0-2 hr) and S2 cells are shown along with HeLa and NIH 3T3 (Chang et al., 2014).

FIG. 3b: Virtual gel image of poly(A) tail length distribution from Drosophila early embryos and S2 cell. The total intensity of each bin (intensity multiplied by area) is proportional to read counts and normalized by each lane.

FIG. 3c Reproducibility between two biological replicates of mTAIL-seq. Rp refers to Pearson correlation coefficient.

FIG. 3d: Global distributions of poly(A) tails at three stages in biological replicates. The median poly(A) tail lengths is 60 nt in immature oocytes, 69 nt in mature oocytes, and 66 nt in activated eggs.

FIG. 3e: Scatter plots showing the correlation between mRNA abundance change and mean poly(A) length change during late oogenesis and egg activation, respectively. For each stage transition, densities of mRNA abundance change and mean poly(A) length change are plotted in upper and right sides of the scatter plot, respectively. Rp refers to Pearson correlation coefficient.

FIG. 3f: Results of high-resolution poly(A) tail assay (Hire-PAT). The signal intensity is normalized to maximum value at each stage, except for osk, the signal of which is fitted into the immature oocyte stage.

FIG. 4a: Schematic illustration of late oogenesis and egg activation in Drosophila. Global poly(A) tail lengths are addressed at three different stages: immature oocyte, mature oocyte, and activated egg. "Stage 9-10 egg chamber," "stage 14 egg chamber," and "unfertilized but activated egg" are indicated as immature oocyte, mature oocyte, and activated egg, respectively. These terms are used throughout the text.

FIG. 4b: Global distributions of poly(A) tails at three stages. The median poly(A) tail lengths is 60 nt in immature oocytes, 75 nt in mature oocytes, and 73 nt in activated eggs.

FIG. 4c: Scatter plots showing the changes of poly(A) tail lengths upon late oogenesis and egg activation, respectively. The mean poly(A) tail lengths from two biological replicates were averaged. The median of mean poly(A) tail lengths is 58 nt in immature oocytes, 76 nt in mature oocytes, and 70 nt in activated eggs.

FIG. 4d: Changes of mRNA abundance upon late oogenesis and egg activation measured by RNA sequencing (RNA-seq).

FIG. 4e: Examples of individual genes. mTAIL-seq tags were plotted in 3-nt-wide bins and then smoothened with a Hanning window (width=5). The frequency along the Y-axis was normalized by the maximum value at each stage. Note that as "read 2" runs up to only 231 cycles, longer poly(A) tails are presented as 231 nt.

FIGS. 5a and 5b illustrate dynamic regulation of poly(A) tails.

FIG. 5a: Classification of transcripts according to the changes of poly(A) tail length into eight groups. (Top left) Fold changes from the average to the poly(A) length of each stage are shown in heat map. The median of the mean poly(A) length of each group is presented in the heat map. Patterns of poly(A) length changes at the individual gene level are presented in the line graphs. Red lines indicate the median.

FIG. 5b: Functional categorization of genes in each group by GO analysis (false discovery rate [FDR]<0.1). For overlapping terms, a representative term is selectively shown.

FIG. 6a: Heat maps showing the distributions of intragenic poly(A) tail lengths in each group. Poly(A) length is discretized with 20 nt wide bins, and the color intensity indicates the fraction of poly(A) tags for the gene. For each heat map, genes are sorted and reordered by geometric mean of poly(A) length (colored line).

FIG. 6b: Poly(A) tail distribution of two representative genes from each group is presented as in FIG. 4e.

FIG. 7a: Reproducibility between two biological replicates of wisp mutant.

FIG. 7b: Violin plots showing the changes of mRNA abundance in wisp mutant at three different stages (*$P<2.2\times 10^{-16}$, two-sided Kolmogorov-Smirnov test). Black line refers to the median.

FIG. 7c: Comparison of poly(A) tail lengths between wild type and wisp mutant in each stage as in FIG. 8a. Dashed line marks 1.5-fold reduction. Turquoise dots indicate mitochondria-related genes.

FIG. 8a: Comparison of poly(A) tail lengths between wild type and the wisp mutant in each stage. The mean poly(A) tail lengths from two biological replicates are averaged. n=2. The median of mean poly(A) tail lengths of wisp mutants is 56 nt in immature oocytes, 34 nt in mature oocytes, and 32 nt in activated eggs. The dashed line marks 1.5-fold reduction. Red dots represent ribosomal protein genes.

FIG. 8b: Wispy-dependent groups in mature oocytes and activated eggs are defined as in A and are presented in the Venn diagram at the left. The gray region contains genes that have dependency on both stages. Orange and red refer to stage-specific genes in mature oocytes and activated eggs, respectively. Genes independent of Wispy are depicted similarly in the Venn diagram at the right.

FIG. 8c: A scatter plot showing the changes of poly(A) tail length in wisp mutants upon late oogenesis.

FIG. 9a: Comparison of poly(A) tail length with TE, which was estimated by Kronja et al. (2014). TE was calculated by dividing ribosome density over RNA abundance from two biological replicates. The median of TE at each stage was adjusted to 0. "Rs" refers to Spearman correlation coefficient.

FIG. 9b: A scatter plot showing the correlation between mean poly(A) length changes and TE changes upon egg activation. "Rp" refers to Pearson correlation coefficient.

FIG. 9c: Translational controls on poly(A) tail length profiles. Violin plots showing the differences in TE changes between eight groups that were defined in FIG. 5a. The poly(A) length changes of each group are simplified in the bottom panel. The black line represents the median.

FIG. 10a: Poly(A) tail lengths of mature oocytes and activated eggs (0-1 hr) are compared to translational efficiency as in FIG. 9a.

FIG. 10b: A scatter plot showing the correlation between mean poly(A) length changes (from mature oocytes to activated eggs [0-1 hr]) and TE changes as in FIG. 9b.

FIG. 10c: Violin plots showing the changes in ratio of polysome fractions (5 ribosomes) to monosome fractions (40S, 60S, and 80S) between activated eggs and mature oocytes. Polysome profiling and RNA-seq were adopted from Kronja et al. (Kronja et al., 2014). Each color indicates a corresponding group defined in FIG. 5a, and poly(A) length changes of each group are simplified in the bottom panel. Black line represents the median.

MODE FOR CARRYING OUT THE INVENTION

Figure 1A:
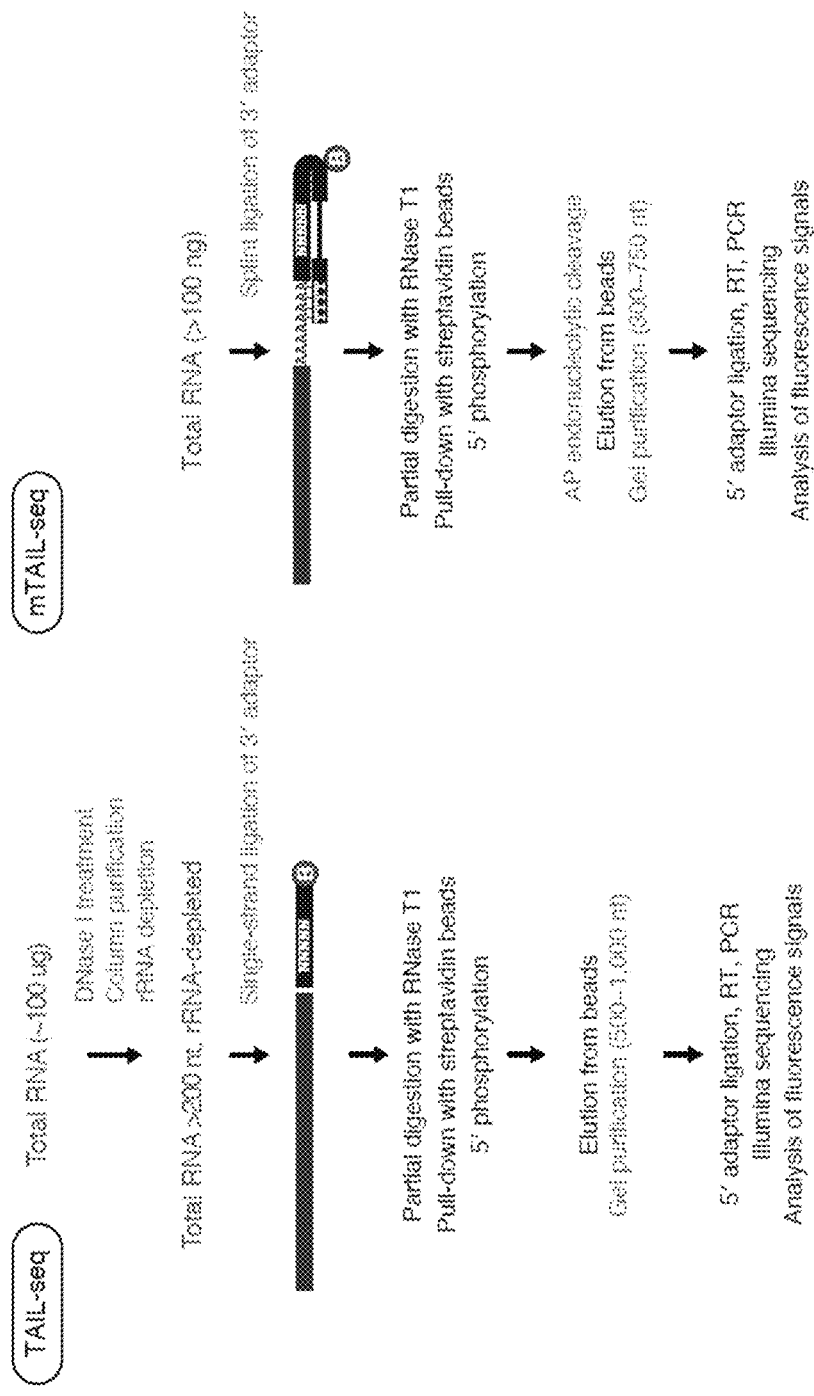
FIGS. 1a-1g illustrate validation of mTAIL-seq.

Hereinafter, the present disclosure will be described in detail with reference to examples. These examples are only for illustrating the present disclosure more specifically, and it will be apparent to those skilled in the art that the scope of the present invention is not limited by these examples.

EXAMPLES

Materials and Methods

Construction of the mTAIL-Seq Library

Total RNAs were extracted from HeLa cells or Drosophila samples by TRIzol reagent (Invitrogen, 15596-018). Total RNA (~1-5 μg) was ligated to a 3' hairpin adaptor using T4 RNA ligase 2 (New England Biolabs, M0239) overnight. 3' ligated RNA was partially digested by RNase T1 (Ambion, AM2283) and subjected to streptavidin beads (Invitrogen, 11206D). 5' phosphorylation by PNK reaction (Takara, 2021B) and endonucleolytic cleavage by APE1 reaction (New England Biolabs, M0282) were performed on beads. Subsequently, RNA was eluted by 2×RNA loading dye and gel-purified by 6% urea-PAGE gel in the range of 300-750 nt. The purified RNAs were ligated to the 5' adaptor, subjected to reverse transcription (Invitrogen, 18080-085), and amplified by FOR using Phusion DNA polymerase (Thermo, F-530L). PCR products were purified by AMPure XP beads (Beckman, A63881).

The library was sequenced on Illumina MiSeq (51×251 paired end run) with 50% of the PhiX control library (Illumina, FC-110-3001) and 10% of the spike-in mixture. The spike-ins were prepared and mixed as previously described (Chang et al. 2014).

TABLE 1

Oligonucleotide sequence for mTAIL-seq

| Name | Sequence |
| --- | --- |
| 5' adaptor | 5'-GUUCAGAGUUCUACAGUCCGACGAUC-3' (SEQ ID NO: 1) |
| 3' hairpin adaptor 1 | 5'-/5Phos/CTGACATGNNNNNNNNNNNNNTGGAATTCTCGGG TGCCAAGGC/iSpC3//idSp//idSp//iBiodT//iBiodT/GGCACCCGAG AATT/iSp18/CATGTCAGTTTTTTTT/3InvdT/-3' (SEQ ID NO: 20) |
| 3' hairpin adaptor 2 | 5'-/5Phos/CTGACATGNNNNNNNNNNNNNTGGAATTCTCGGG TGCCAAGGC/iSpC3//idSp//idSp//iBiodT//iBiodT/GGCACCCGAG AATT/iSp18/CATGTCAGATTTTTTT/3InvdT/-3' (SEQ ID NO: 21) |
| 3' hairpin adaptor 3 | 5'-/5Phos/CTGACATGNNNNNNNNNNNNNTGGAATTCTCGGG TGCCAAGGC/iSpC3//idSp//idSp//iBiodT//iBiodT/GGCACCCGAG AATT/iSp18/CATGTCAGAATTTTTT/3InvdT/-3' (SEQ ID NO: 22) |
| RT primer | 5'-GCCTTGGCACCCGAGAATTCCA-3' (SEQ ID NO: 2) |
| PCR primer (forward) | 5'-AATGATACGGCGACCACCGAGATCTACACGTTCAGAGTTCTA CAGTCCGA-3' (SEQ ID NO: 3) |
| PCR primer (reverse) 1 | 5'-CAAGCAGAAGACGGCATACGAGATCGTGATGTGACTGGAGT TCCTTGGCACCCGAGAATTCCA-3' (SEQ ID NO: 4) |
| PCR primer (reverse) 2 | 5'-CAAGCAGAAGACGGCATACGAGATACATCGGTGACTGGAGT TCCTTGGCACCCGAGAATTCCA-3' (SEQ ID NO: 5) |
| PCR primer (reverse) 3 | 5'-CAAGCAGAAGACGGCATACGAGATGCCTAAGTGACTGGAGT TCCTTGGCACCCGAGAATTCCA-3' (SEQ ID NO: 6) |
| PCR primer (reverse) 4 | 5'-CAAGCAGAAGACGGCATACGAGATTGGTCAGTGACTGGAGT TCCTTGGCACCCGAGAATTCCA-3' (SEQ ID NO: 7) |

TABLE 1-continued

Oligonucleotide sequence for mTAIL-seq

| Name | Sequence |
|---|---|
| PCR primer (reverse) 5 | 5'-CAAGCAGAAGACGGCATACGAGATCACTGTGTGACTGGAGTTCCTTGGCACCCGAGAATTCCA-3' (SEQ ID NO: 8) |
| PCR primer (reverse) 6 | 5'-CAAGCAGAAGACGGCATACGAGATATTGGCGTGACTGGAGTTCCTTGGCACCCGAGAATTCCA-3' (SEQ ID NO: 9) |
| PCR primer (reverse) 7 | 5'-CAAGCAGAAGACGGCATACGAGATGATCTGGTGACTGGAGTTCCTTGGCACCCGAGAATTCCA-3' (SEQ ID NO: 10) |
| FOR primer (reverse) 8 | 5'-CAAGCAGAAGACGGCATACGAGATTCAAGTGTGACTGGAGTTCCTTGGCACCCGAGAATTCCA-3' (SEQ ID NO: 11) |
| PCR primer (reverse) 9 | 5'-CAAGCAGAAGACGGCATACGAGATTACAAGGTGACTGGAGTTCCTTGGCACCCGAGAATTCCA-3' (SEQ ID NO: 12) |
| Spike-in_0 | 5'-TCAGAGTTCTACAGTCCGACGATCNNNNNNNNNNNNNNNNNNNNNNNCTGACGAGCTACTGTTGGAATTCTCGGGTGCCA-3' (SEQ ID NO: 13) |
| Spike-in_8 | 5'-TCAGAGTTCTACAGTCCGACGATCNNNNNNNNNNNNNNNBAAAAAAAACTGACGAGCTACTGTTGGAATTCTCGGGTGCCA-3' (SEQ ID NO: 14) |
| Spike-in_16 | 5'-TCAGAGTTCTACAGTCCGACGATCNNNNNNNNNNNNNNNBAAAAAAAAAAAAAAAACTGACGAGCTACTGTTGGAATTCTCGGGTGCCA-3' (SEQ ID NO: 15) |
| Spike-in_32 | 5'-TCAGAGTTCTACAGTCCGACGATCNNNNNNNNNNNNNNNBAAAAAAAAAAAAAAAAAAAAAAAAAAAAAAAACTGACGAGCTACTGTTGGAATTCTCGGGTGCCA-3' (SEQ ID NO: 16) |
| Spike-in_64 | 5'-TCAGAGTTCTACAGTCCGACGATCNNNNNNNNNNNNNNNBAAAAAAAAAAAAAAAAAAAAAAAAAAAAAAAAAAAAAAAAAAAAAAAAAAAAAAAAAAAAAAAACTGACGAGCTACTGTTGGAATTCTCGGGTGCCA-3' (SEQ ID NO: 17) |
| Spike-in_118 | 5'-TCAGAGTTCTACAGTCCGACGATCNNNNNNNNNNNNNNNBAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAACTGACGAGCTACTGTTGGAATTCTCGGGTGCCA-3' (SEQ ID NO: 18) |
| Spike-in_128 | 5'-TCAGAGTTCTACAGTCCGACGATCNNNNNNNNNNNNNNNBAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAACTGACGAGCTACTGTTGGAATTCTCGGGTGCCA-3' (SEQ ID NO: 19) |

N refers to a random sequence, /5Phos/ refers to 5' phosphorylation, /iSpC3/ refers to internal 03 phosphoramidite, /idSp/ refers to internal 1,2'-dideoxyribose, /iBiodT/ refers to internal biotinylated deoxythymidine, /iSp18/ refers to an internal 18-atom hexaethyleneglycol spacer, and /3InvdT/ refers to 3' inverted deoxythymidine.

mTAIL-Seq Analysis

The detailed procedure of poly(A) length measurement was identical to that of TAIL-seq (Chang et al. 2014) except for variations in usage of the 3' hairpin adaptor. FIG. 1g illustrates an example of the analysis procedure for poly(A) length measurement. Genes with 50 poly(A) tags were analyzed. A geometric mean of poly(A) lengths was used as a representative value and is referred as "mean poly(A) length" because a distribution of intragenic poly(A) lengths is a lognormal-like distribution. For replicates, the average of geometric mean lengths was used in analyses.

Drosophila Stocks and Oocyte/Egg Collection

Fly lines of $w^{1118}$ and $wisp^{KG5287}$ were obtained from the Bloomington Drosophila Stock Center, and $tud^1$ was from the Kyoto Stock Center. $w^{1118}$ was used as a wild-type control. $wisp^{KG5287}$ was previously described as a null allele of wisp (Benoit et al. 2008). Immature (stage 9-10) and mature (stage 14) egg chambers were collected by hand dissection in Grace's unsupplemented insect medium (Gibco, 11595-030) from 3- or 4-d-old female flies. Unfertilized activated eggs were produced from w[1118] virgin females mated to sterile males (sons of tud[1] mothers) (Boswell and Mahowald 1985). Fly eggs and embryos were collected on grape juice plates for the designated time frame at 25° C.

RNA-Seq Analysis

Total RNA was extracted with TRIzol (Invitrogen, 15596-018), and the quality was checked by an Agilent 2100 Bioanalyzer. rRNA was depleted from total RNA using a Ribo-Zero kit (Epicentre, MRZH11124). RNA-seq libraries were constructed by Macrogen, Inc., using Illumina TruSeq RNA sample preparation kit version 2. Sequencing reads derived from cDNA libraries described above were processed by using FASTX-Toolkit (www.hannonlab.cshl.edu/lastx_toolkit). First, the 3' adaptor sequence was removed, and trimmed reads were filtered by Phred quality score (fastq_quality_filter -Q 33 -p 30 -q 90). The sequence reads were aligned to ERCC RNA spike-ins using STAR version 2.4.2a (Dobin et al. 2013) with options—alignIntronMin 99999 -alignEndsType EndToEnd. Reads that did not match to any spike-in were aligned to UCSC (University of California at Santa Cruz) dm6 genome assembly using RSEM version 1.2.25 with STAR (Li and Dewey 2011; Dobin et al. 2013), and splicing junction annotations were generated from the NCBI RefSeq (downloaded from UCSC Genome Browser on Dec. 12, 2014). The reduced RefSeq transcript set for nonoverlapping representation was prepared as previously described (Chang et al. 2014). The reads mapped to ERCC spike-ins were counted by using htseqcount (Anders et al. 2015). Next, the expected counts from RSEM (Li and Dewey 2011) were normalized with spike-ins by using RUVg (k=1) in R package RUVSeq (Risso et al. 2014). For analysis, transcripts with insufficient reads (<100 normalized reads in any library) were removed.

Classification and Functional Categorization of Genes

We classified genes based on the difference of poly(A) tail lengths between consecutive developmental stages. First, genes with a <20-nt difference across three stages were regarded as an unchanged group (group 8). Next, we set a 10-nt difference between the adjacent two stages as a criteria to discriminate changes of poly(A) tail length: elongated or shortened (10 nt difference) or unchanged (<10 nt difference). A group showing elongation of poly(A) tails in late oogenesis and shortening in egg activation was further subdivided into two groups depending on the value of sgn (elongated length or shortened length). Additionally, three groups with shortened poly(A) tails in late oogenesis were merged, since each group had a small number of members. Functional annotation was done for each gene group using DAVID bioinformatics tools (Huang da et al. 2009). For the background population, members of all groups (3664 genes) were used, and GO terms with false discovery rate (FDR) <0.1 were selected.

Ribosome Profiling Analysis

RPF (ribosome profiling) and RNA-seq data were downloaded from a publicly available database (GSE52799) (Kronja et al. 2014). Sequencing reads were trimmed into 27-nt-long sequences and then filtered with Phred quality score. RPF and RNA-seq tags were counted and normalized by using RSEM (Li and Dewey 2011). To minimize a tendency from ribosomes accumulating near the start codon, reads with 5' ends mapping within the first 50 nt of each ORF were disregarded (Ingolia et al. 2009; Subtelny et al. 2014). TE was calculated by the TPM (transcripts per million) ratio of RPF to RNA-seq, and the median of log 2(TE) was adjusted to 0. Genes with 0 TPM in both RPF and RNA-seq libraries were included in the analysis.

Accession Numbers

Sequencing data have been deposited in the NCBI Gene Expression Omnibus (GEO) database (accession no. GSE83732).

Results mTAIL-Seq: A Solution for Limited Materials

For the original version of TAIL-seq, a large amount of total RNA (~100 μg) was needed to achieve enough sequencing depth for mRNA (FIG. 1a, left; Chang et al. 2014). In order to improve the sensitivity, we decided to use splint ligation, which allowed us to capture RNAs with a specific type of terminus. Note that we did not use oligo(dT) affinity purification so as to avoid a potential bias toward long poly(A) tails. Splint ligation has been used to generate various cDNA libraries, and it has been shown that splint ligation does not cause a significant bias over a wide range of poly(A) tails except for very short A tails (less than ~8 nt) (Subtelny et al. 2014).

Figure 1B:
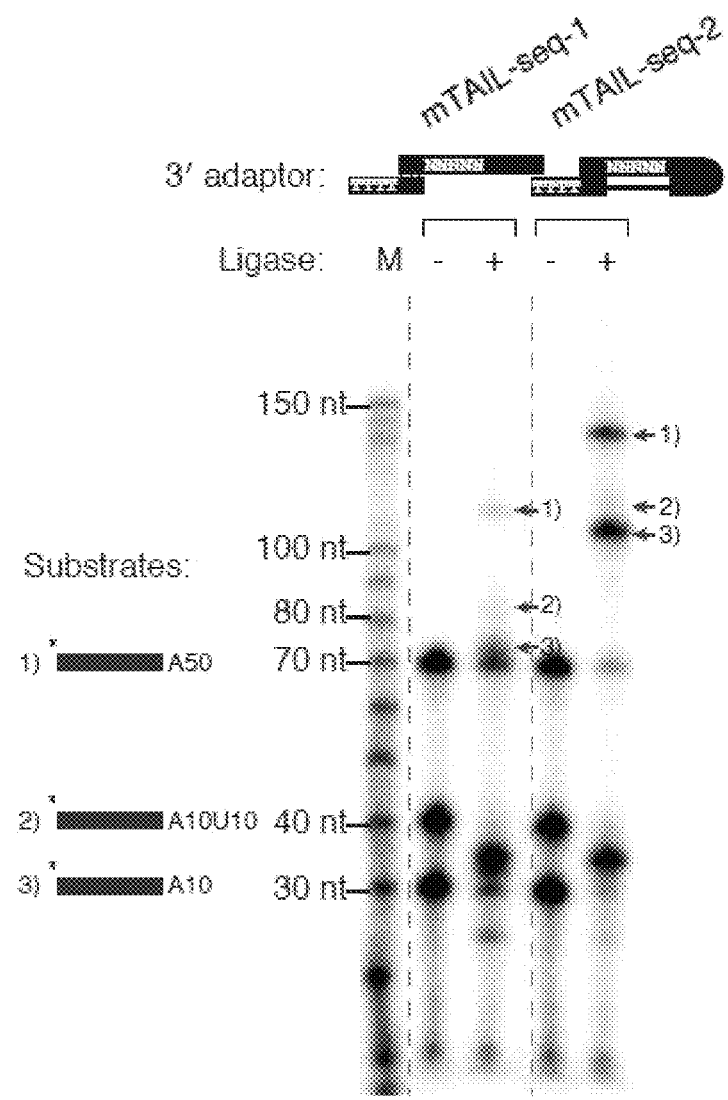
Figure 2A:
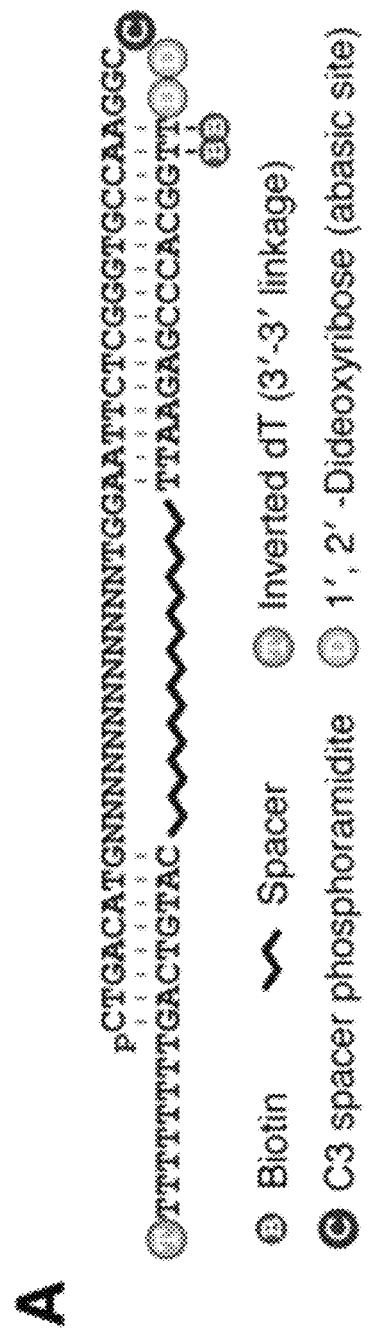
FIGS. 2a-2f illustrate design and performance of mTAIL-seq.
Figure 2B:
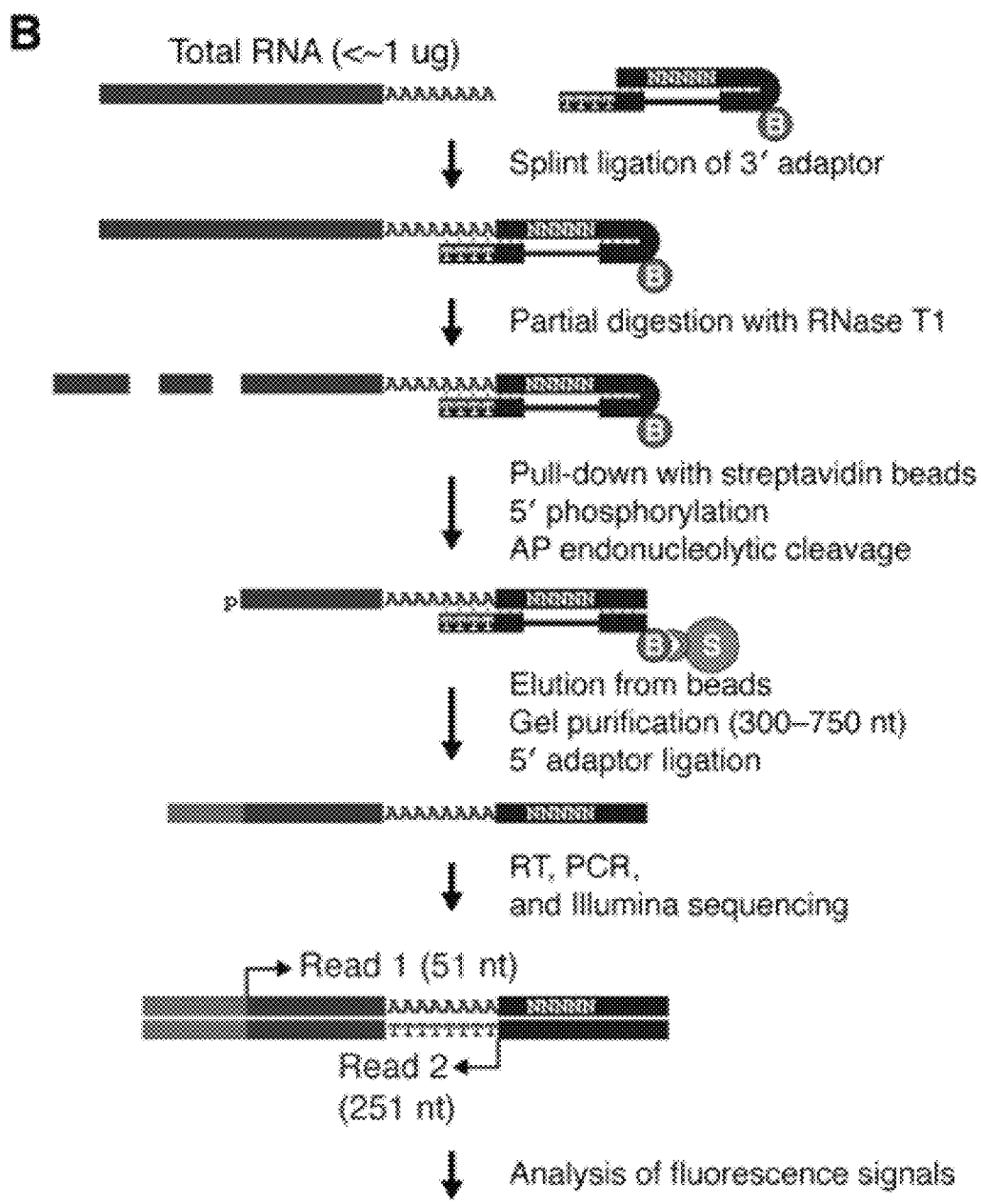
Figure 2C:
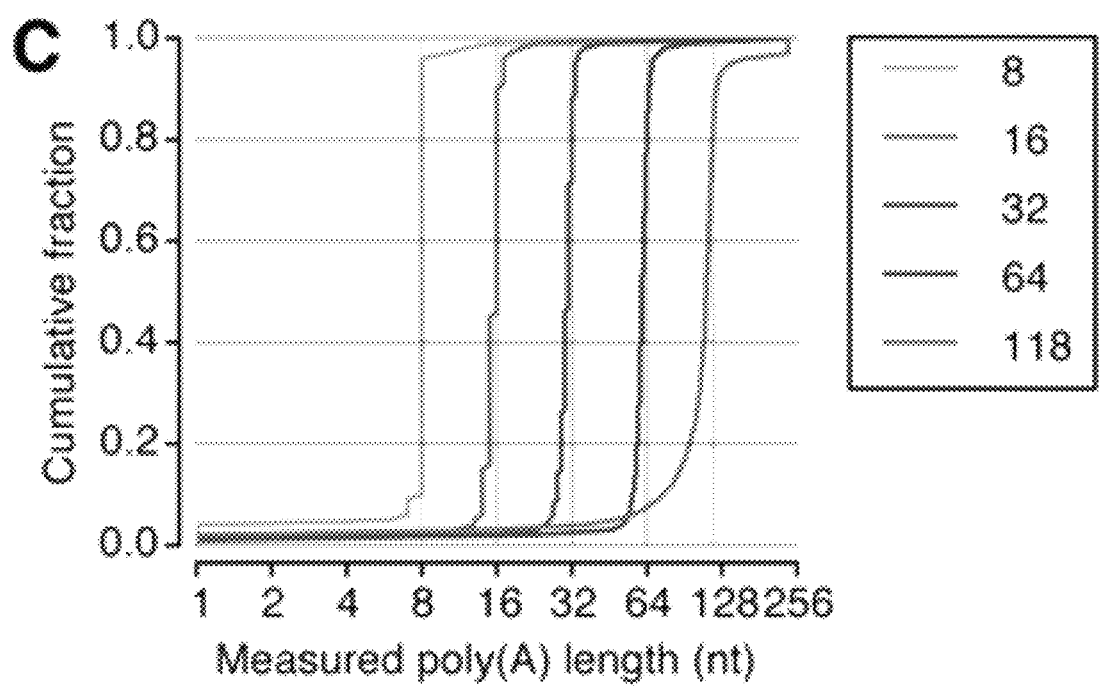

For splint ligation, stable annealing of the bridge oligo and the 3' adaptor was a major issue because the TAIL-seq 3' adaptor contains degenerate sequences that are used to improve sequencing performance and monitor uneven amplification (Chang et al. 2014). Initially, we used splint ligation in a conventional way that uses a bridge oligo between the 3' adaptor and target RNA (FIG. 1b, mTAIL-seq-1). However, ligation efficiency was poor due to weak base-pairing between the 3' adaptor and bridge. To stably anchor the bridge to the 3' adaptor, we designed a hairpin adaptor instead of using two single-stranded oligos (FIG. 2a; FIG. 1b, mTAIL-seq-2). The intervening random sequences are bypassed by an ethylene glycol spacer. We confirmed that ligation was efficient and specific to A-tailed substrates (FIG. 1b).

mTAIL-seq has several distinct features in the library construction procedure (FIG. 2b; FIG. 1a). First, the 3' hairpin adaptor specifically captures poly(A)+ RNA, so we can omit the rRNA depletion step, which is expensive and time-consuming. Second, the 3' hairpin adaptor has two abasic sites that can easily be cut by apurinic/apyrimidinic endonuclease 1 (APE1). The cleavage helps elution of the ligated RNA from the bead and allows reverse transcription by releasing the opposite strand. Third, we changed the range of size fractionation from 500-1000 nt to 300-750 nt to increase gel elution efficiency. The remaining steps of library preparation and data analysis are similar to the previous version, with minor changes. We validated the performance of the mTAIL-seq analysis pipeline by using spike-ins of known poly(A) tail length (FIG. 2c).

Figure 1C:
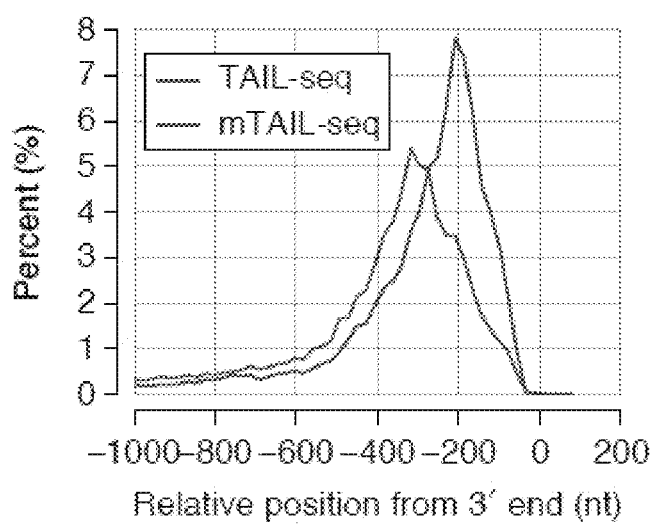
Figure 1D:
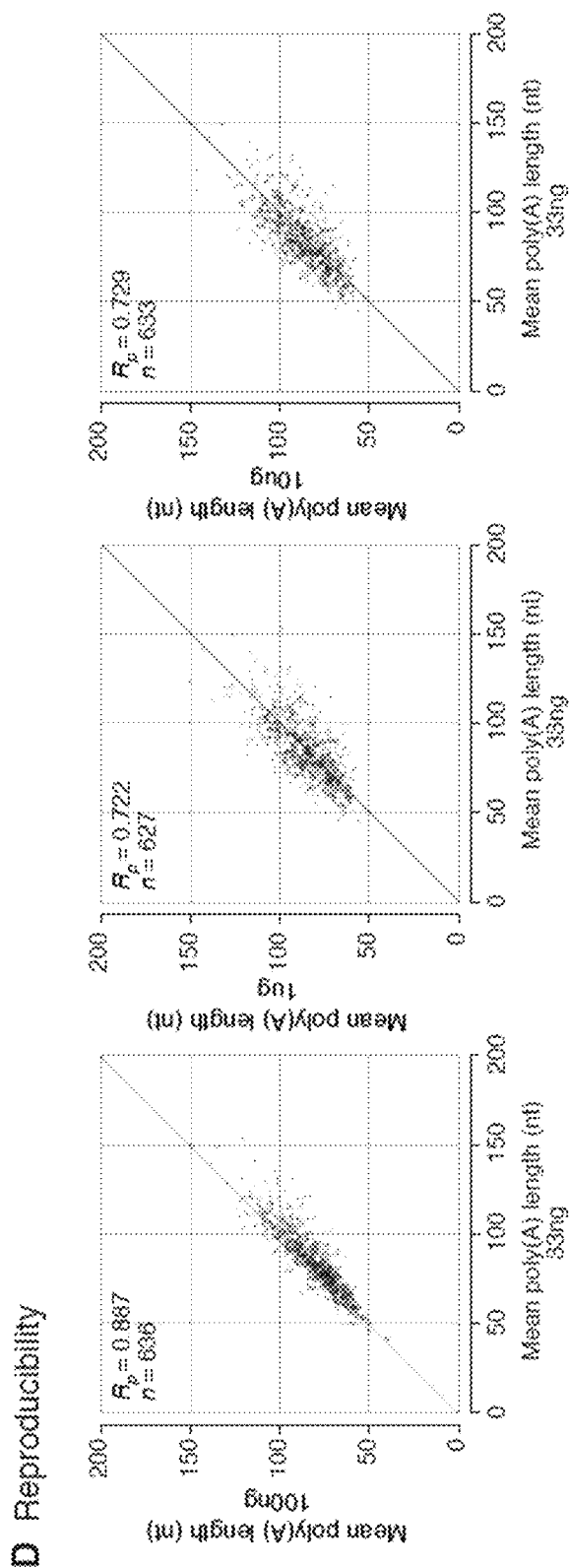
Figure 2D:
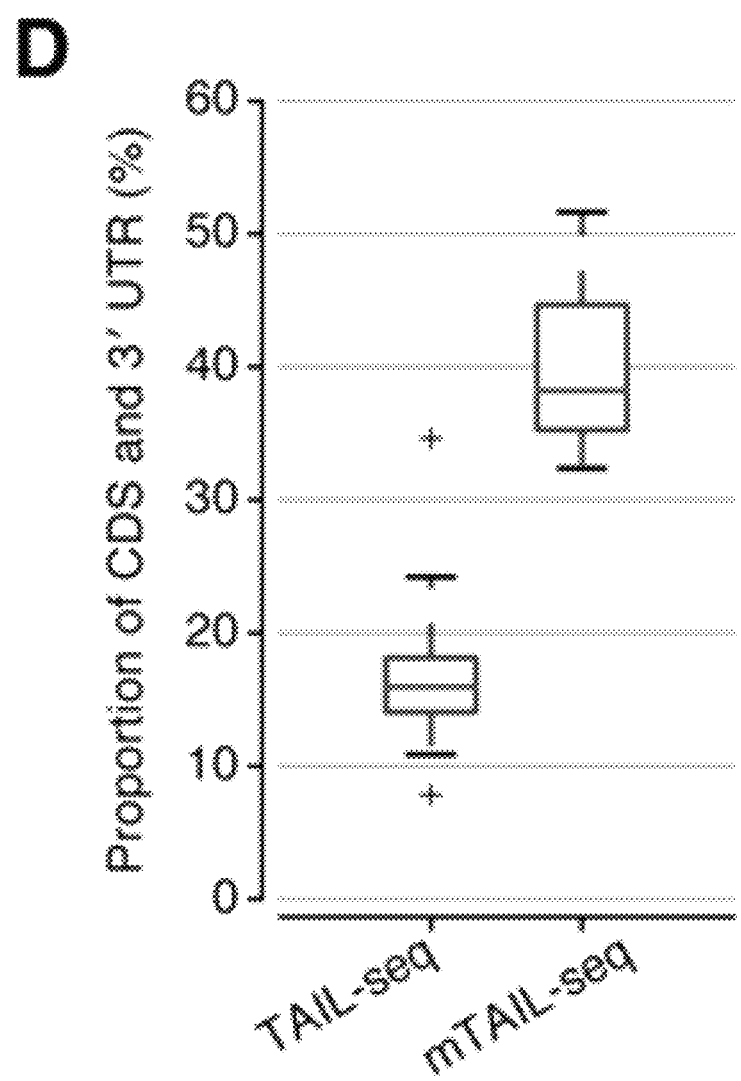
Figure 2E:
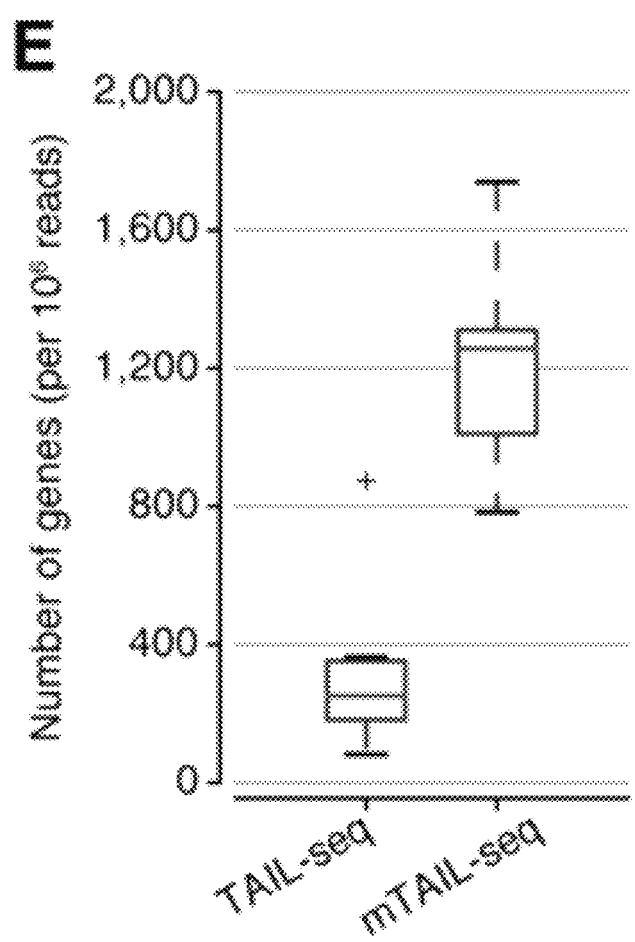
Figure 2F:
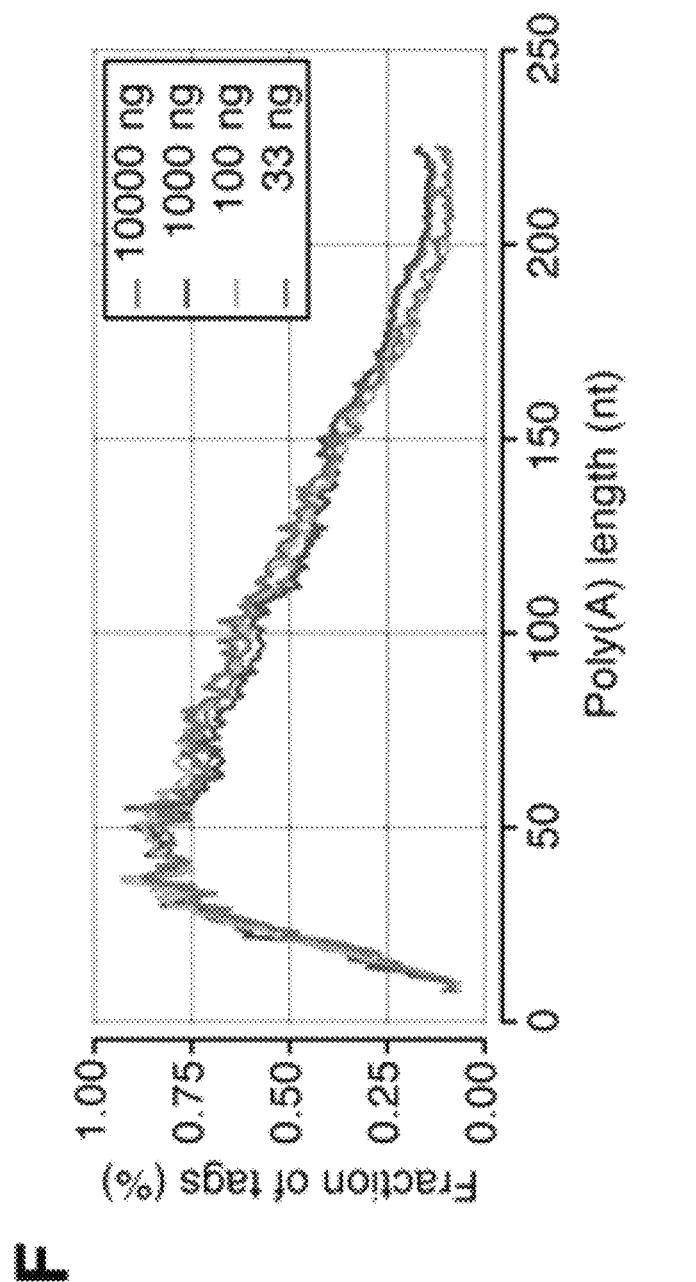

Compared with TAIL-seq, mTAIL-seq provided significantly more mRNA reads that are mapped to coding sequences (CDSs) and 3' UTRs (FIG. 2d). Expectedly, the tags were derived mainly from near the annotated 3' ends (FIG. 1c). In terms of sensitivity, mTAIL-seq detected ~1250 genes per million reads on average, which is approximately five times greater than the original TAIL-seq (FIG. 2e). It allowed us to analyze thousands of genes even from a small scale run on Illumina MiSeq, which reduces the cost of sequencing. It is noteworthy that mTAIL-seq detected 643 genes with at least 50 poly(A)+ tags even from 33 ng of total RNA, which corresponds to ~1000 HeLa cells. Four experiments covering a broad dynamic range of input RNA showed reproducible results, indicating that mTAIL-seq is a robust technique (FIG. 2f; FIG. 1d).

Figure 1E:
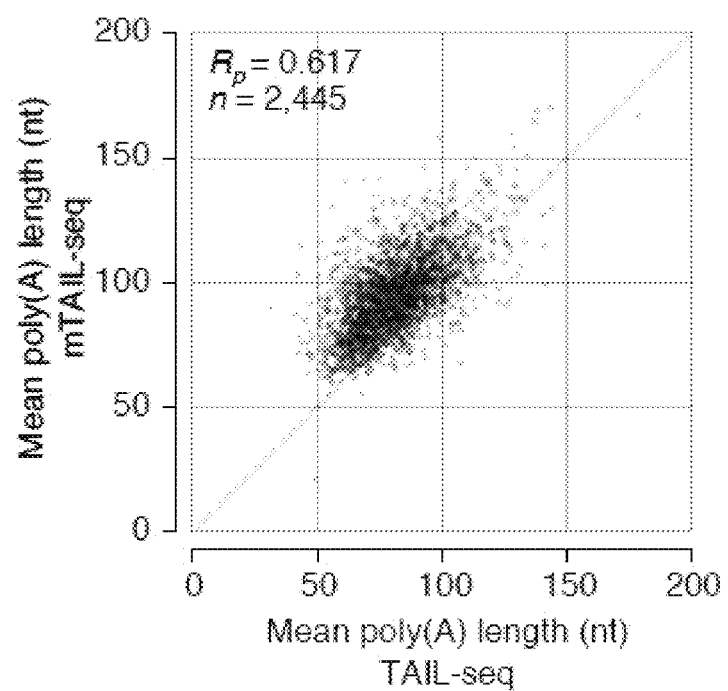
Figure 1F:
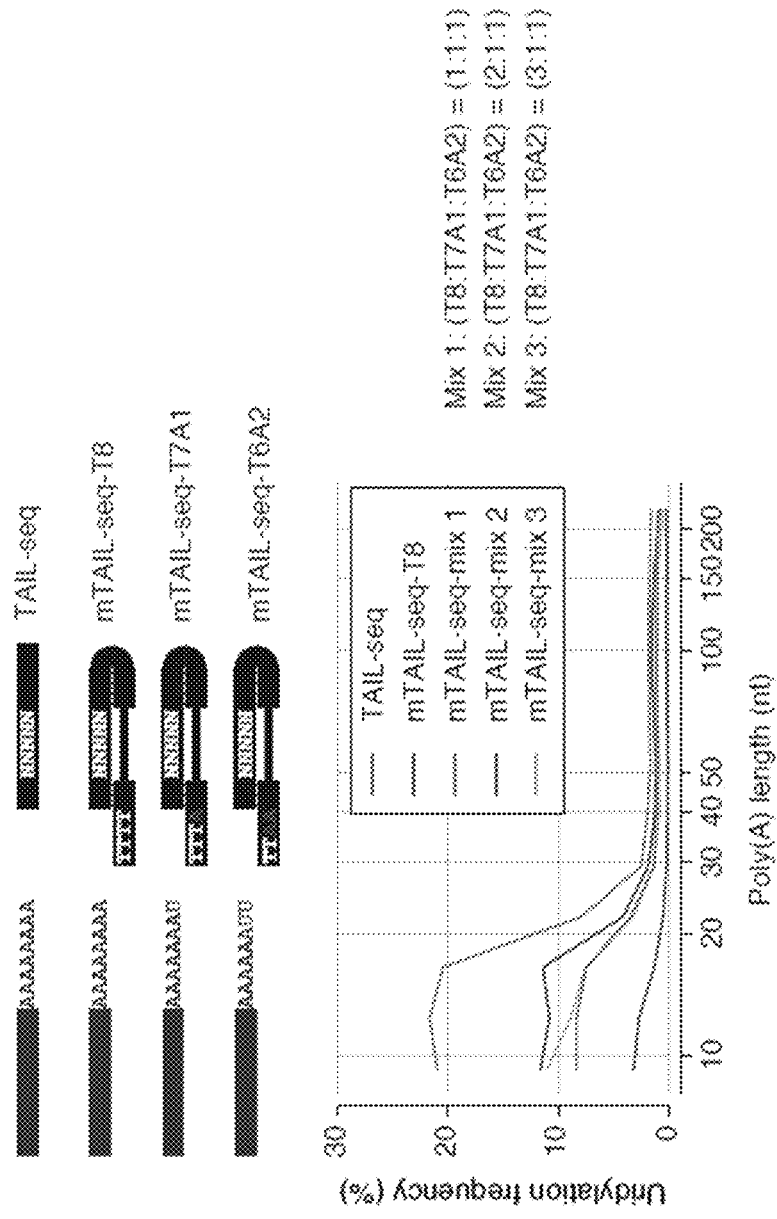
Figure 1G:
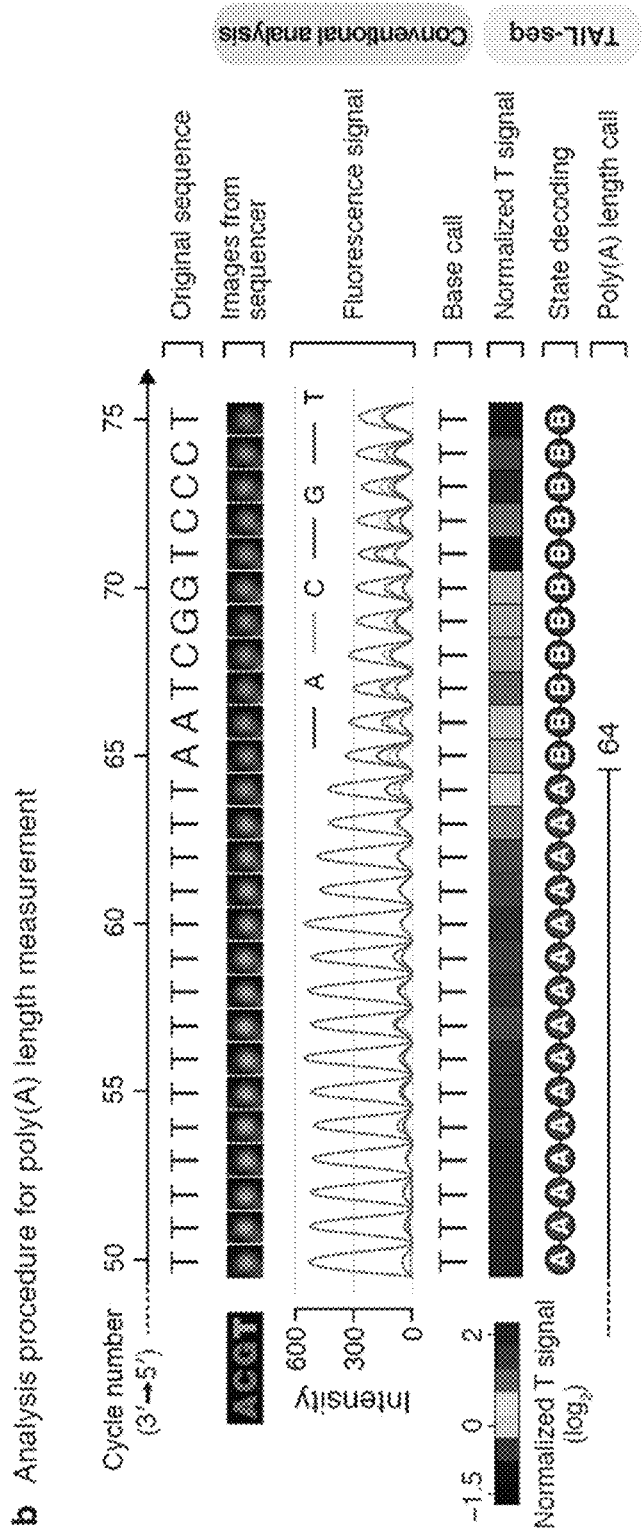

As expected, mTAIL-seq provides longer median lengths than TAIL-seq (FIG. 1e) because the splint ligation used in mTAIL-seq cannot capture certain types of tails such as very short A tails (below 8 nt) or those with 3' modifications. Uridylation is the most frequent modification of poly(A) tails and is found mainly on short tails <25 nt (Chang et al. 2014; Lim et al. 2014). Monouridylation and diuridylation are the most prevalent uridylation types. Since uridylated tails are not efficiently ligated to the adaptor with eight Ts (FIG. 1f, mTAIL-seq-T8), we sought to capture uridylated tails by synthesizing and mixing two additional hairpin adaptors that carry one or two adenosines at the overhang (FIG. 1f, mTAIL-seq-T7A1 and mTAIL-seq-T6A2). With the mixture of adaptors, we could detect uridylated tails, albeit at a lower frequency as compared with original TAIL-seq (FIG. 1f). Thus, mTAIL-seq is adjustable to enrich a specific type of terminus by changing the design of adaptors with different sequences.

In conclusion, both TAIL-seq and mTAIL-seq have unique strengths suitable for particular purposes. TAIL-seq offers a comprehensive view of the 3' terminome that covers all types of RNA termini. On the other hand, mTAIL-seq can be more practical if one is interested in a specific type of RNA terminus, such as poly(A)+ mRNAs. For its enhanced sensitivity and reduced cost and time, mTAIL-seq is useful especially when only a small amount of biological sample is available and/or when many samples need to be analyzed and compared.

Global Poly(A) Tail Length Measurement in Drosophila

Figure 3A:
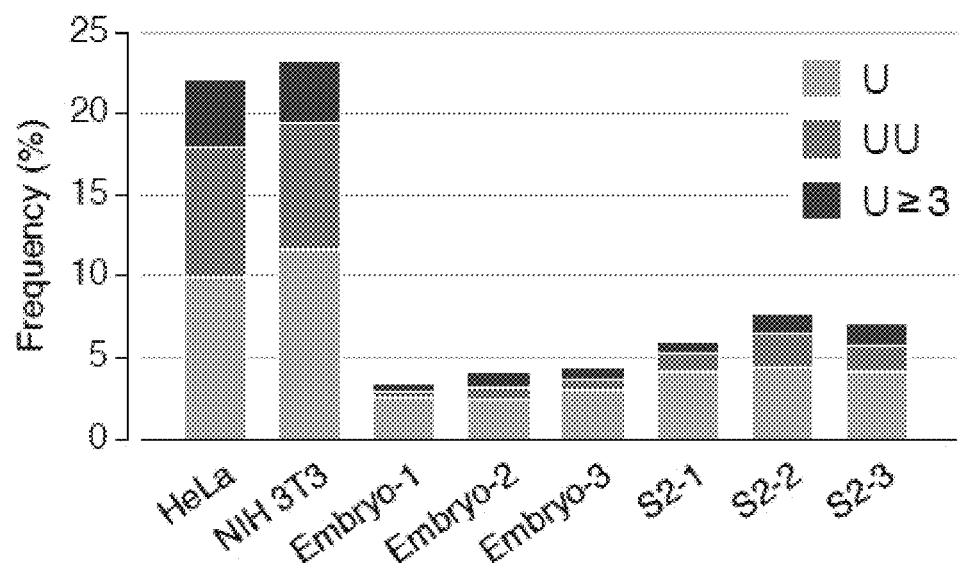
FIGS. 3a-3f illustrate poly(A) tail length profiles and 3' uridylation rate of Drosophila samples.

Previous studies on cytoplasmic polyadenylation focused mainly on specific individual mRNAs with critical roles in developmental processes. In this study, to gain a transcriptomic landscape of cytoplasmic polyadenylation, we applied mTAIL-seq on Drosophila oocytes and embryos. Of note, we initially used the original TAIL-seq protocol for Drosophila early embryos (0-2 h after egg laying [AEL]) and S2 cells, which are relatively easy to obtain in a sufficient quantity. We found that the uridylation frequency in these samples is far lower than that in HeLa and NIH3T3 cells, which implies that uridylation may play a limited role in flies (FIG. 3a).

Figure 3B:
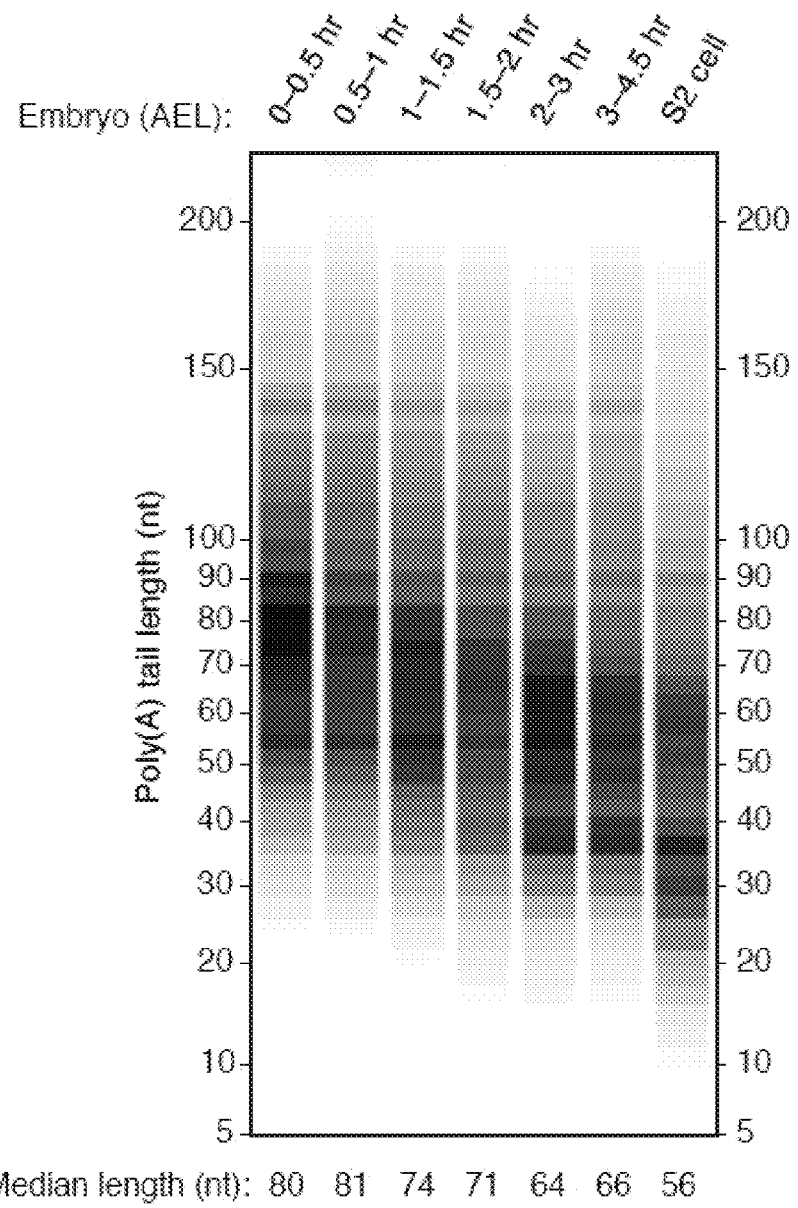

Using mTAIL-seq with a T8 adaptor, we monitored poly (A) tail length at six different time points during early embryo development, ranging from 0 to 4.5 h AEL (FIG. 3b). Because major activation of zygotic transcription occurs ~2 h AEL, the samples up to 2 h AEL represent an early stage of development at which transcription is silenced (Tadros and Lipshitz 2009). We expected that poly(A) tail length would increase globally as described in fertilized eggs of Xenopus and zebrafish (Subtelny et al. 2014), but, surprisingly, the median length of poly(A) tails of early embryos did not significantly increase in the 0- to 2-h period, implying that poly(A) tail elongation may occur at an earlier stage prior to fertilization in flies (FIG. 3b).

Figure 3C:
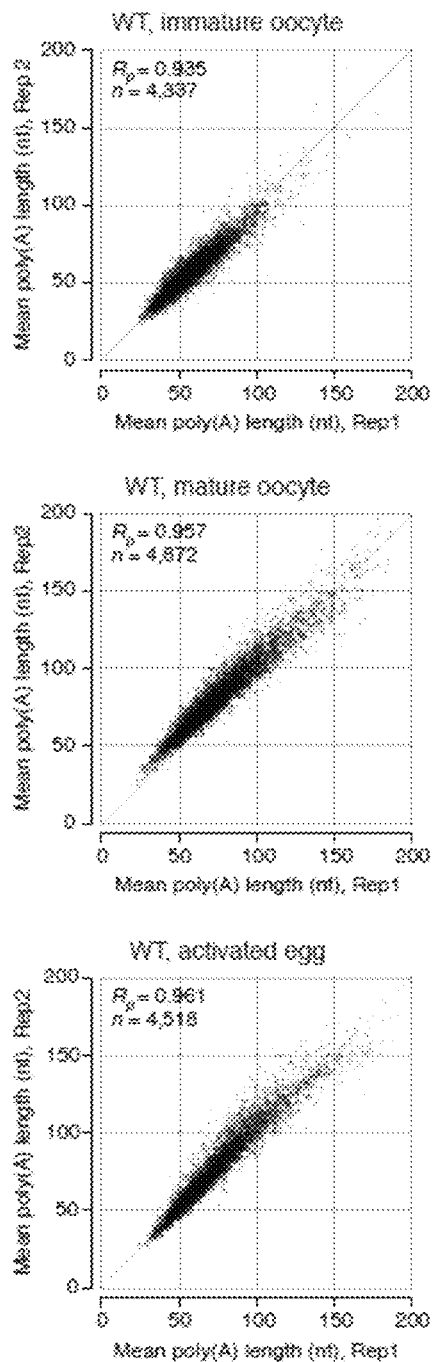
Figure 4A:
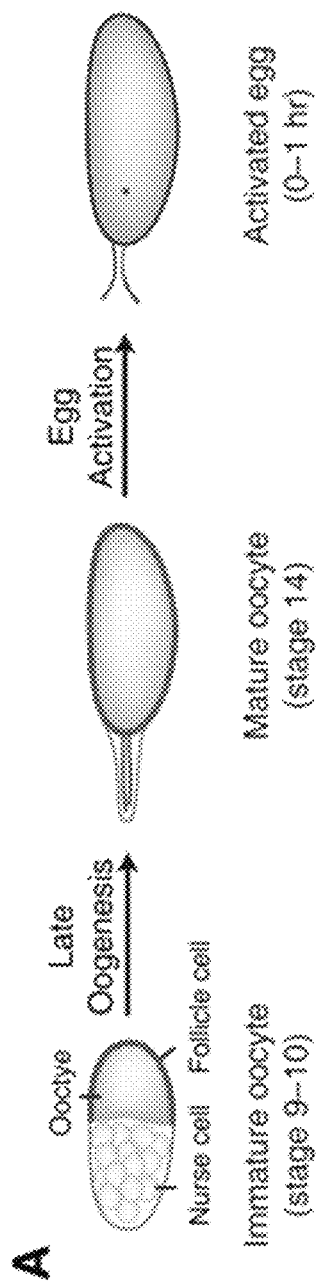
FIGS. 4a-4e illustrate global lengthening of poly(A) tails during Drosophila oogenesis.

To determine the developmental stage at which cytoplasmic polyadenylation takes place, we examined three stages of female gametes: immature oocyte (stage 9-10 egg chamber), mature oocyte (stage 14 egg chamber), and activated egg (0-1 h AEL) (FIG. 4a; Bastock and St Johnston 2008; He et al. 2011). Drosophila ovarian development comprises 14 distinct stages. Two critical events, oocyte maturation and egg activation, are required for the production of functional embryos. At stage 9-10, each egg chamber contains one immature oocyte and 15 nurse cells. Nurse cells provide maternal mRNAs and proteins to the oocyte and break down shortly after this stage. At around stage 12-13, the immature oocyte undergoes maturation to yield metaphase I-arrested mature oocytes a metaphase I-arrested mature oocyte (stage 14) (Resnick et al. 2009; Von Stetina and Orr-Weaver 2011; Laver et al. 2015). The mature oocyte is ovulated from the ovary and pass through the reproductive tract, which triggers egg activation and exit from meiosis. In Drosophila, egg activation is induced by mechanical pressure independent of fertilization (Heifetz et al. 2001; Homer and Wolfner 2008). Thus, we collected activated but unfertilized eggs for 1 h after they were laid instead of fertilized embryos. This allowed us to examine maternal mRNAs upon egg activation, avoiding the compounding effects from zygotic transcription. From small amounts of oocyte and egg samples (corresponding to <5 µg of total RNA), we performed mTAIL-seq with MiSeq and measured the poly (A) tail length of 3664 genes [with at least 50 poly(A)+ tags in all three samples]. Two biological replicates at each stage showed a high degree of reproducibility (FIG. 3c).

Figure 3D:
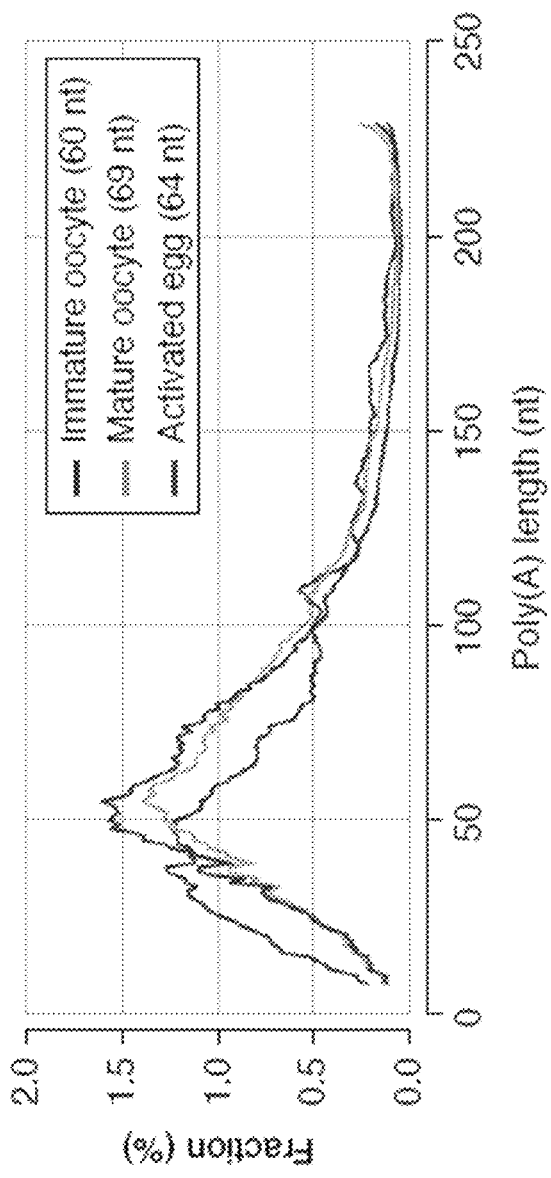
Figure 3E:
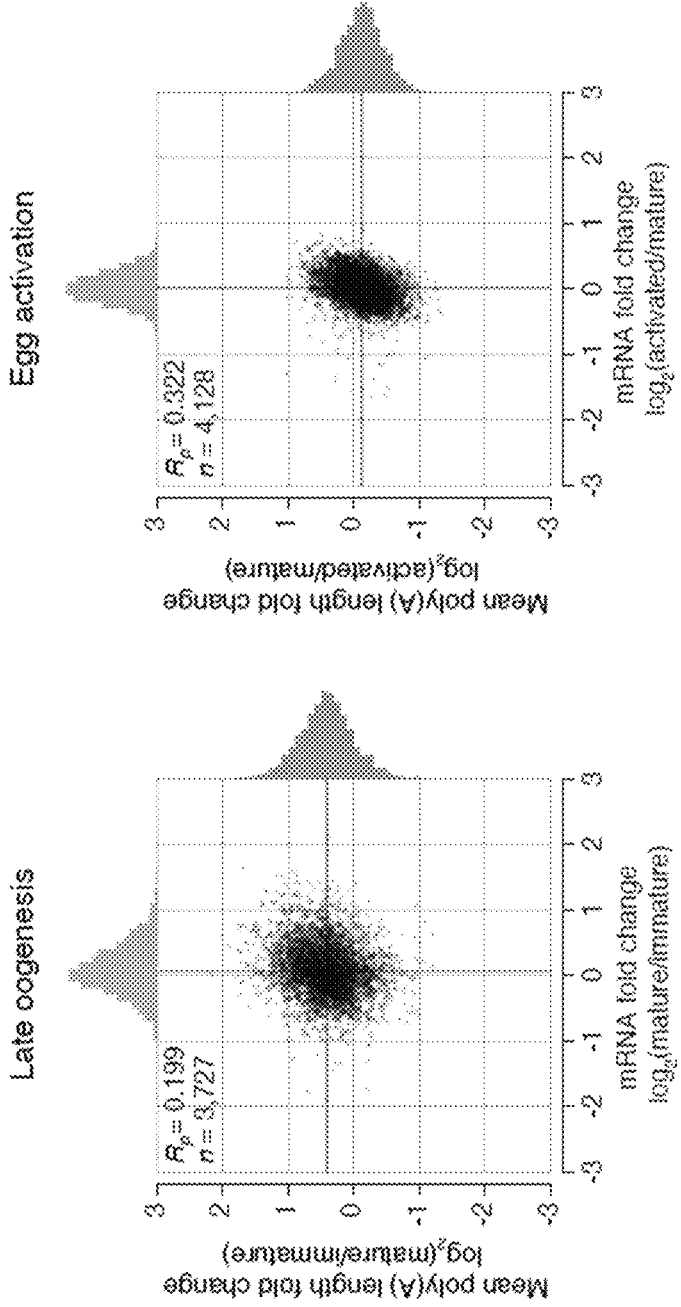
Figure 4B:
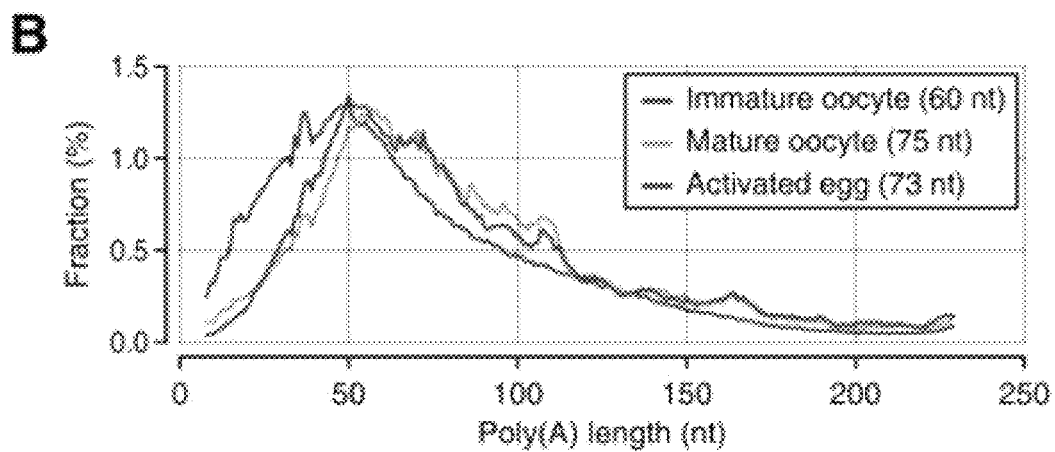
Figure 4C:
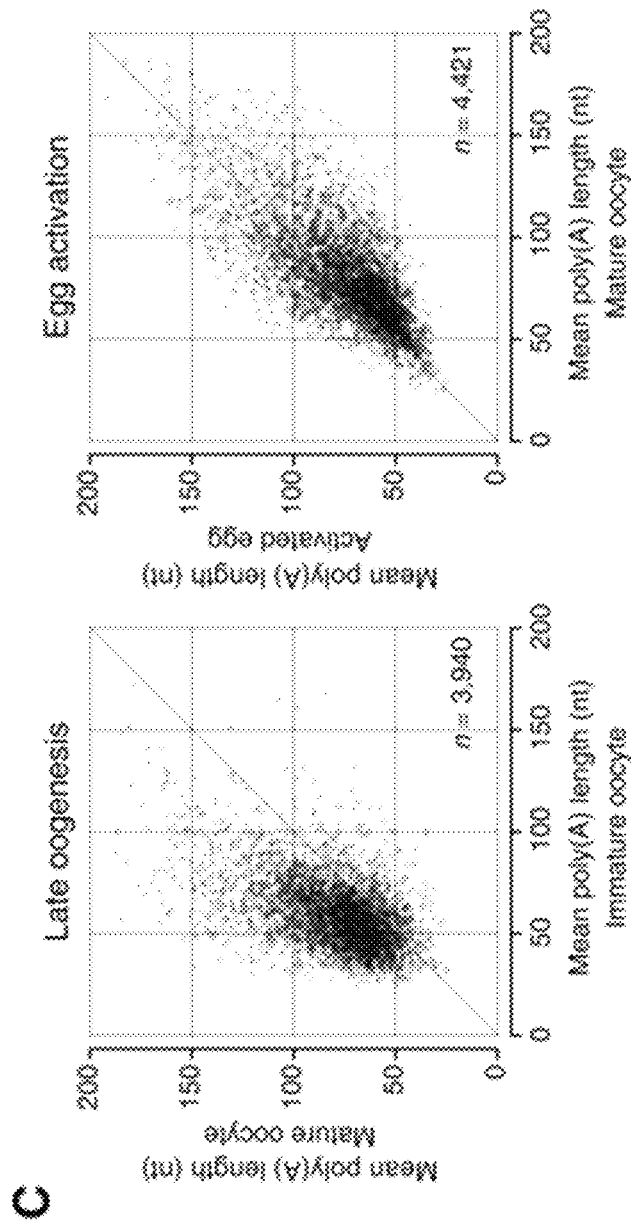
Figure 4D:
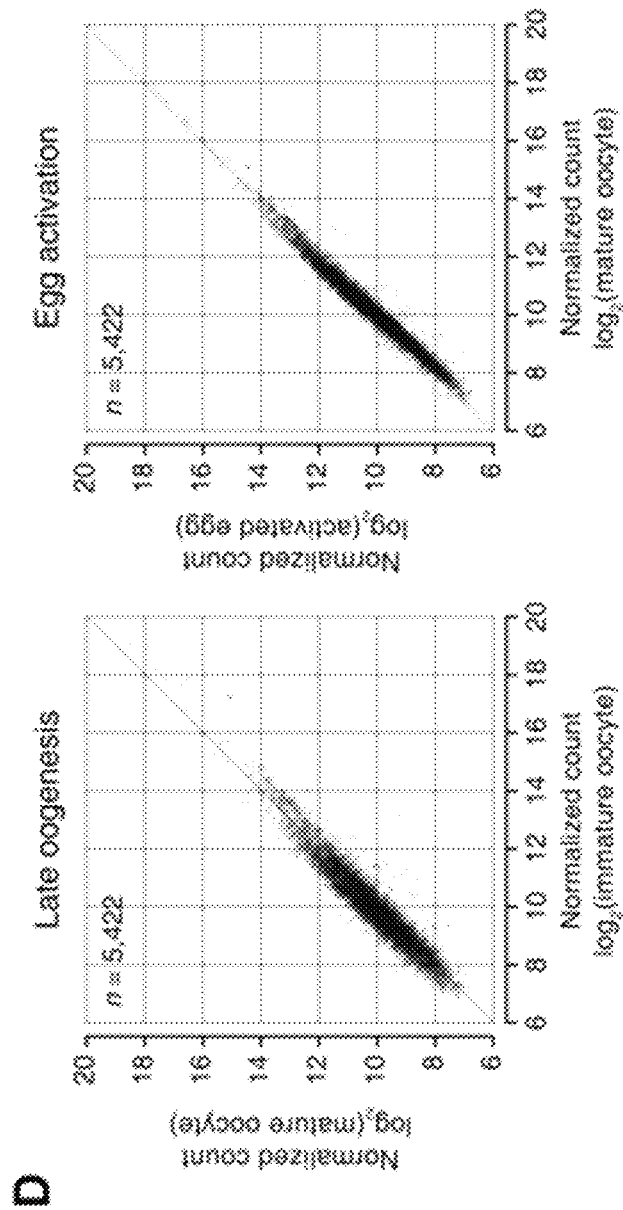

Interestingly, we observed a drastic difference in poly(A) length distribution between immature oocytes and mature oocytes, while only a minor change was seen between mature oocytes and activated eggs (FIG. 4b; FIG. 3d). The median length in the global profile increased from 60 nt in immature oocytes to 75 nt in mature oocytes (FIG. 4b). At the gene level, most mRNA species (3365 out of 3940 genes, 85.4%) were polyadenylated during late oogenesis (FIG. 4c, left). The median of mean increased from 58 nt to 76 nt. For most genes, cytoplasmic polyadenylation is initially activated at oocyte maturation in Drosophila, as reported for some genes like cycB and c-mos in Xenopus (Sheets et al. 1994). In contrast, upon egg activation, the median length did not increase at the global level (median: 73 nt; median of mean: 70 nt) (FIG. 4b, c), although there were some gene-specific modulations (FIG. 4c, right). To confirm that this dramatic change of poly(A) tails during late oogenesis was not due to transcription, we performed RNA sequencing (RNAseq) on the same samples used for mTAIL-seq and found that individual mRNA abundance was largely unchanged during late oogenesis and egg activation (FIG. 4d). Additionally, there was no substantial correlation between mRNA abundance change and poly (A) length change (FIG. 3e). Taken together, these analyses indicate that the changes of poly(A) tail length may be caused by cytoplasmic polyadenylation, not nascent transcription.

Figure 3F:
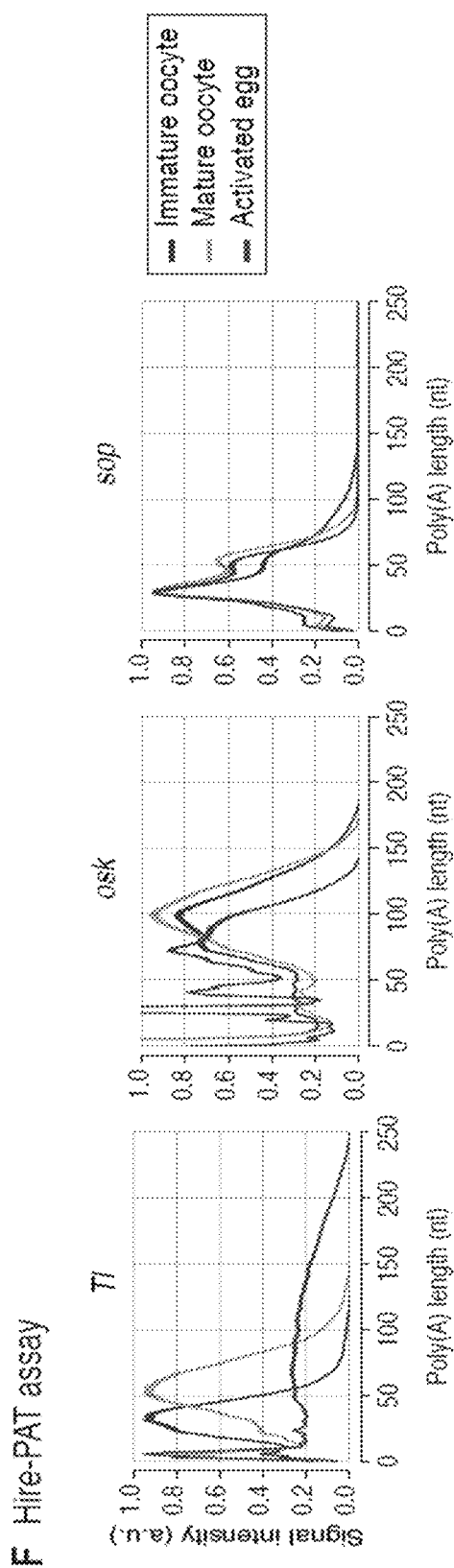
Figure 4E:
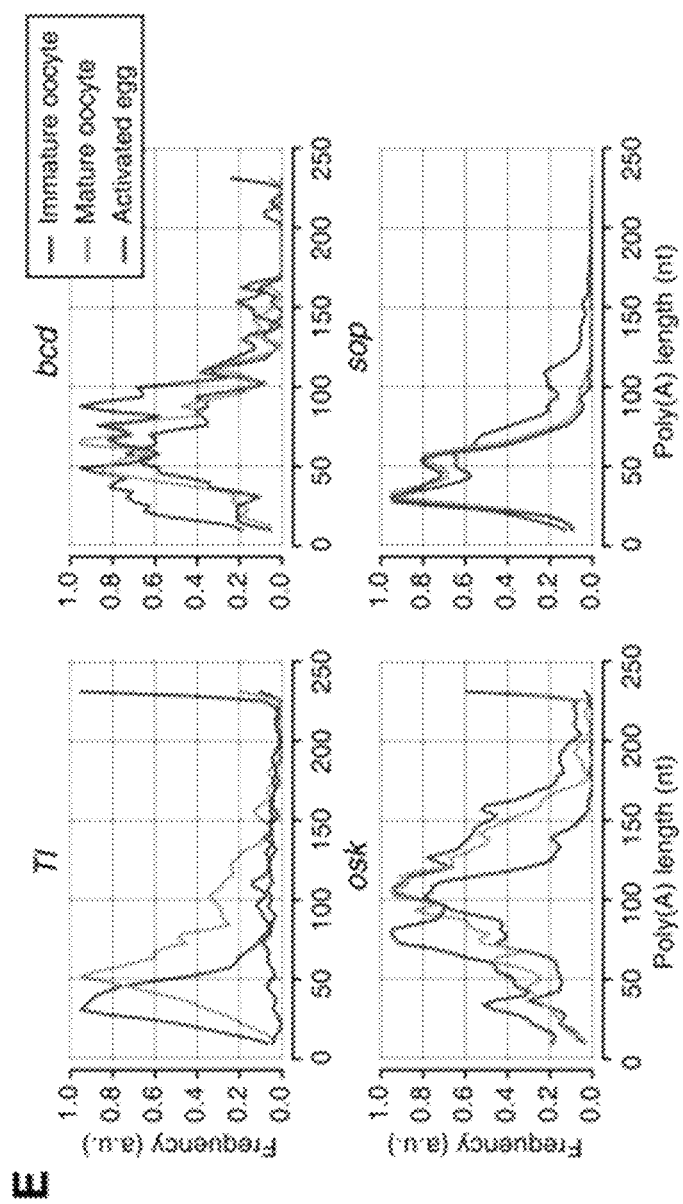

For validation, we next examined several individual genes that were previously studied (FIG. 4e; Salles et al. 1994; Benoit et al. 2005, 2008; Vardy and Orr-Weaver 2007; Vardy et al. 2009). The mTAIL-seq results were validated by high-resolution poly(A) tail (Hire-PAT) assay (FIG. 3f; Bazzini et al. 2012). As expected, embryo patterning-related genes, such as TI and bcd, showed a dramatic increase of poly(A) tail length during late oogenesis and egg activation, whereas sop (ribosomal protein S2) remained nearly unchanged. In the case of embryo posterior determinant osk, the poly(A) tail was relatively long in immature oocytes and mature oocytes, which differs from the previous report showing elongation at this stage (Benoit et al. 2005). However, given the earlier studies reporting the presence of Osk protein in immature oocytes (Kim-Ha et al. 1995; Yoshida et al. 2004) and the enhancement of osk translation by cytoplasmic polyadenylation at the posterior pole before late oogenesis (Castagnetti and Ephrussi 2003), it is likely that the osk mRNA indeed has a long tail and is actively translated in immature oocytes. Therefore, adenylation of some mRNAs may occur prior to stage 9-10.

In conclusion, our mTAIL-seq experiments provide an accurate profile of poly(A) length at the genomic level, revealing dynamic regulation of poly(A) tails during Drosophila oogenesis and egg activation.

Distinct Patterns of Poly(A) Tail Regulation

Figure 5A:
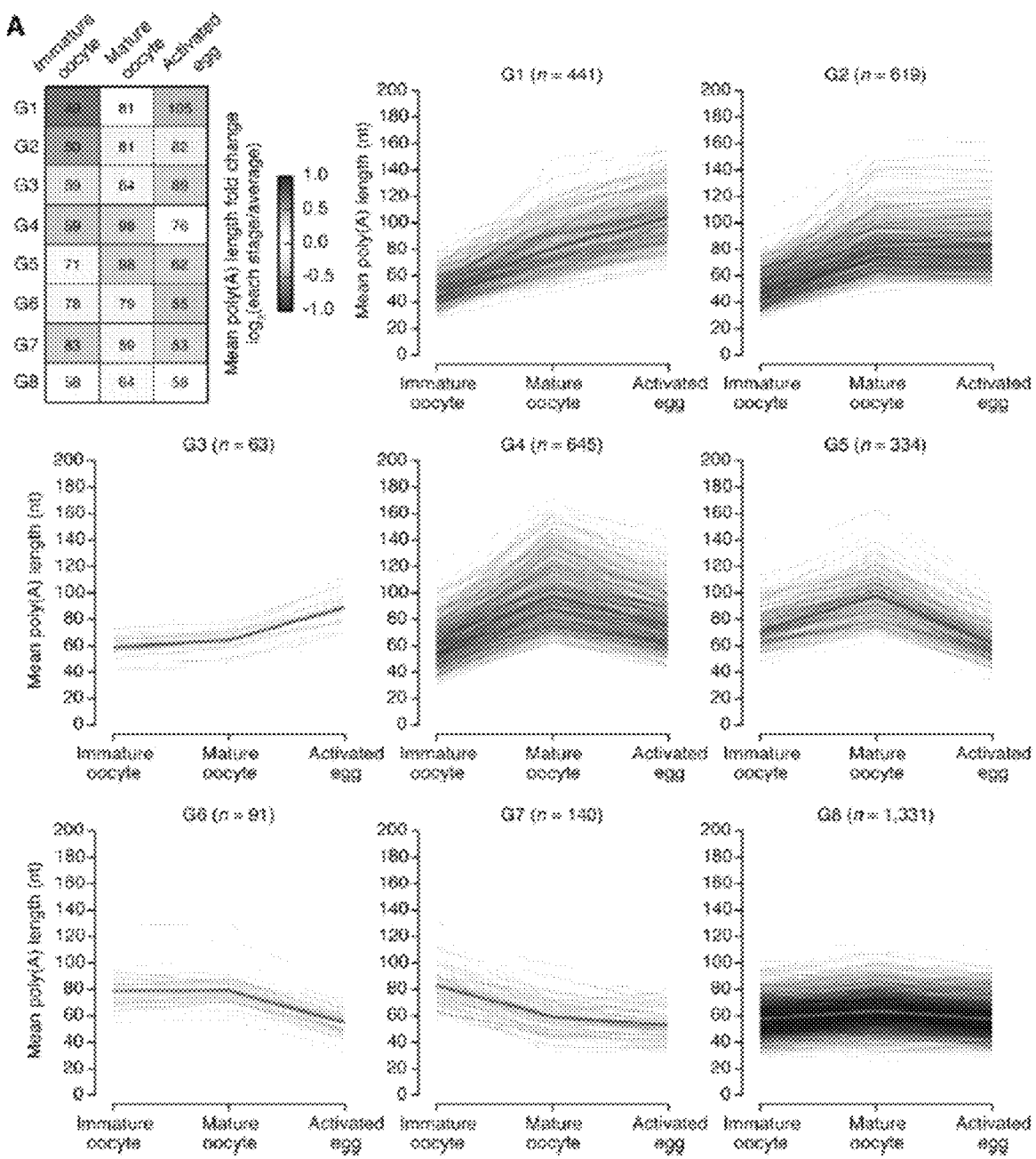
Figure 6A:
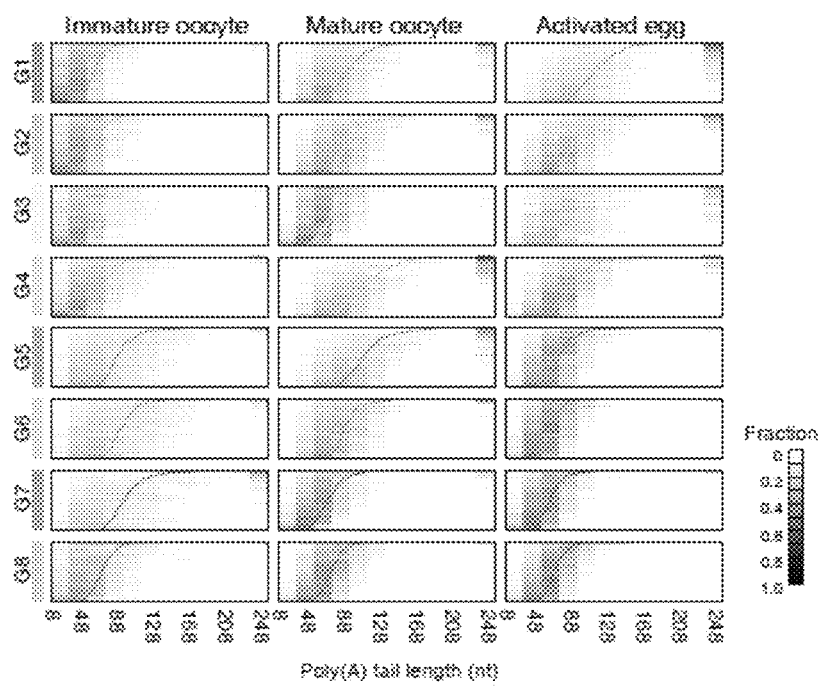
FIGS. 6a and 6b illustrate intragenic poly(A) tail length distributions in two replicates.
Figure 6A:
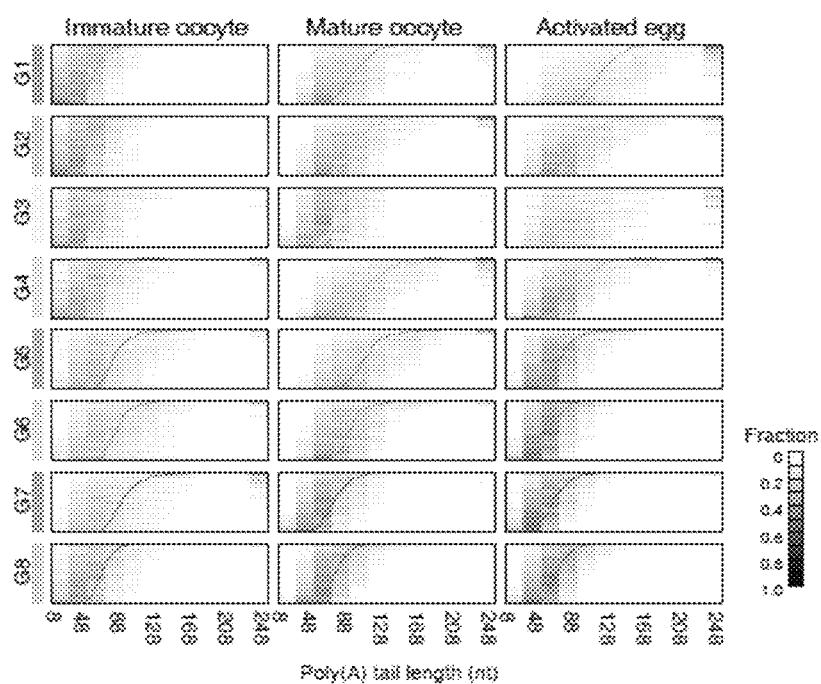
Figure 6B:
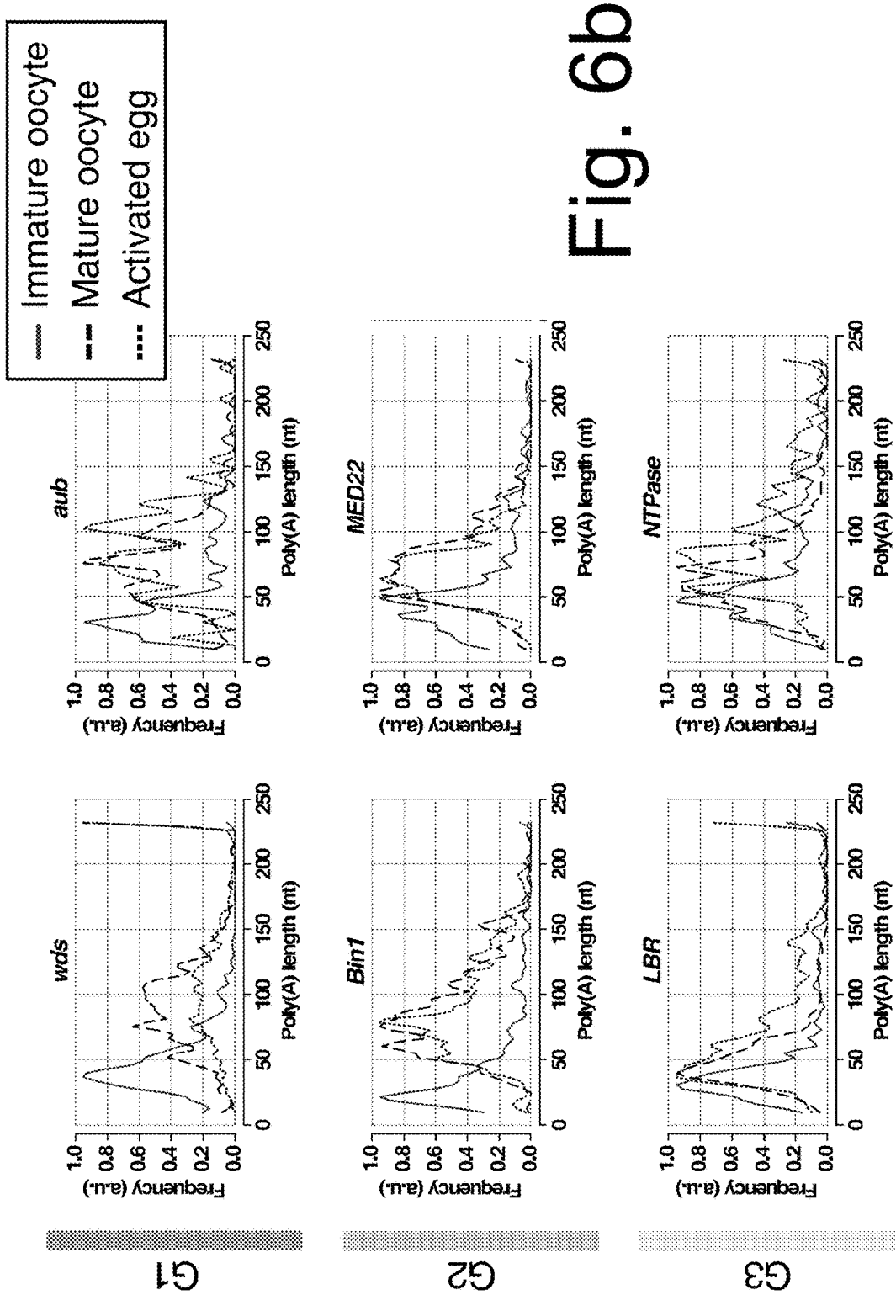
Figure 6B:
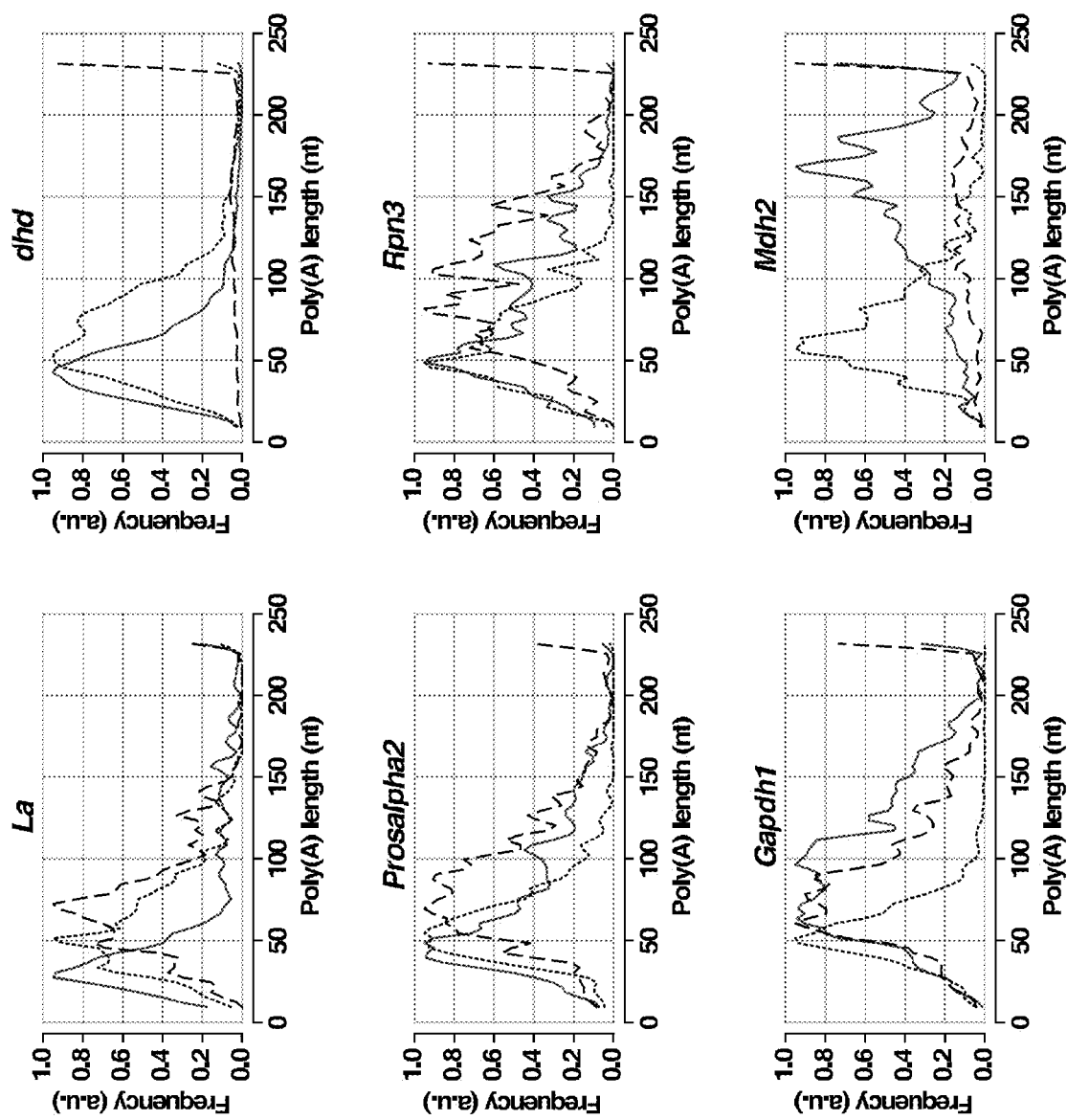
Figure 6B:
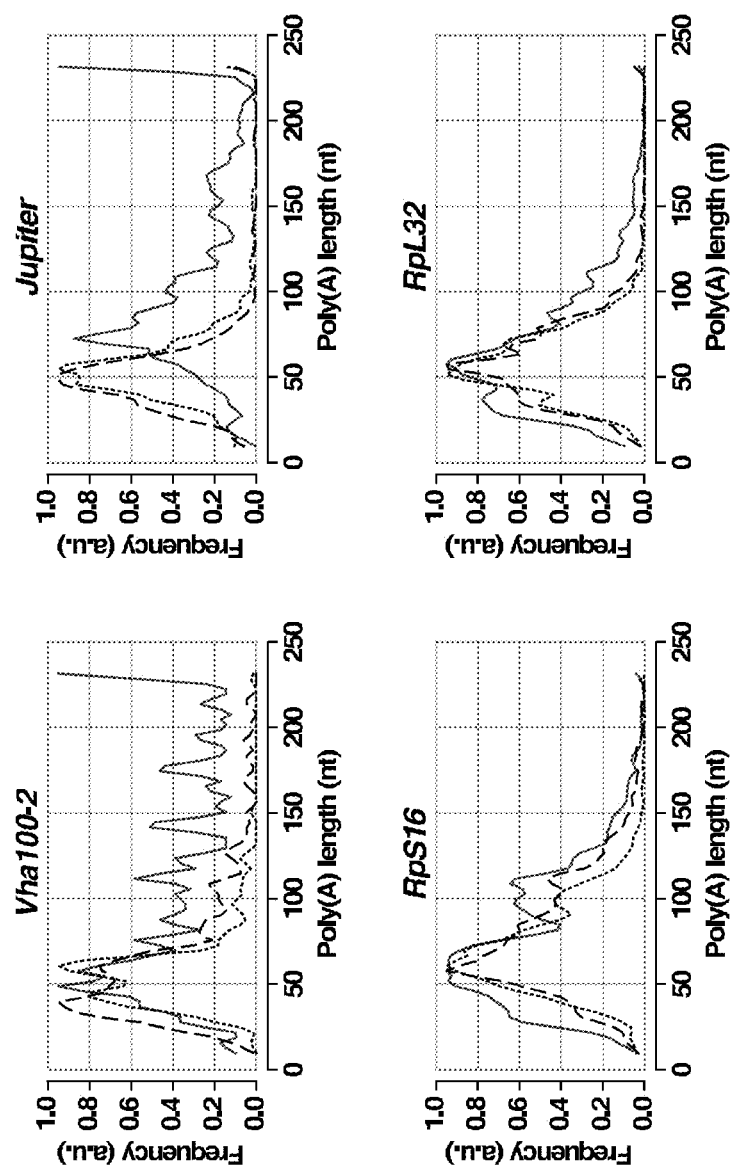

Although poly(A) tail length increases during late oogenesis and is maintained during egg activation at the global level, many individual genes show interesting temporal regulation patterns. Based on these dynamic changes, we classified 3664 genes into eight groups (FIG. 5a; FIG. 6a, b). Groups 1, 2, and 3 show an increase throughout late oogenesis and egg activation. Transcripts in these groups have considerably shorter poly(A) tails at the immature oocyte stage than other transcripts. Specifically, group 1 contains 441 transcripts whose poly(A) tails increase continuously throughout late oogenesis and egg activation. The median length of the poly(A) tails changed from 49 nt to 105 nt. This group includes several well-known targets of cytoplasmic polyadenylation such as TI, bcd, and cycB, which is consistent with previous studies (Salles et al. 1994; Benoit et al. 2005, 2008; Vardy and Orr-Weaver 2007; Vardy et al, 2009). Interestingly, gene ontology (GO) analysis of group 1 reveals enrichment for terms such as "regionalization," "wing disc development," "zinc ion binding," and "regulation of RNA metabolic processes" (FIG. 5b). It is tempting to speculate that group 1 may include some unknown developmental regulators that are poised to act in the early embryo through cytoplasmic polyadenylation.

Next, groups 4 and 5 show fluctuating patterns: lengthening during late oogenesis and shortening during egg activation. Thus, transcripts in these groups are polyadenylated specifically during late oogenesis and undergo deadenylation afterward. What stops their polyadenylation and triggers deadenylation upon egg activation is interesting but unclear at this point. Groups 4 and 5 consist of functionally diverse genes, but many of them encode proteins involved in proteolysis and oxidative phosphorylation. These proteins may need to be transiently produced in mature oocytes and silenced in early embryos immediately following egg activation.

Groups 6 and 7 show descending patterns (FIG. 5a). Transcripts in these groups have relatively long poly(A) tails in immature oocytes (78 nt and 83 nt for group 6 and group 7, respectively) as compared with those in other groups (58 nt for all detected genes). It is possible that these transcripts are cytoplasmically adenylated earlier (before and at stage 9-10) than other transcripts. Alternatively, but not mutually exclusively, the transcripts in groups 6 and 7 may retain their long tails by resisting deadenylation in immature oocytes. Group 6 is enriched with genes related to the generation of precursor metabolites and energy. Rapid deadenylation of these metabolic genes suggests that metabolic pathways may need to be reprogrammed at the onset of animal development.

Group 8 shows little changes in poly(A) tail length profile (<20 nt difference across three stages). This group is enriched with genes with constitutive functions such as ribosomal subunits and translation (FIG. 5b).

To understand the mechanism underlying the selectivity of cytoplasmic polyadenylation, we searched for sequence motifs enriched in each group. However, the analysis did not reveal any known motifs, such as CPEs (data not shown). While vertebrate CPEs are well known to play a central role in coordinating cytoplasmic polyadenylation, the role of Drosophila CPEs remains unclear. Although a fly homolog of CPEB, Orb, was reported to physically and genetically interact with a homolog of GLD-2, Wispy, during oogenesis (Benoit et al. 2008), CPE sequences have not been found commonly in Wispy target mRNAs (Coll et al. 2010; Cui et al. 2013). We suspect that the control of poly(A) tail length may be governed by multiple sequence motifs working in combination as opposed to one master regulatory element, such as CPE.

Cytoplasmic Polyadenylation by Wispy

Figure 7A:
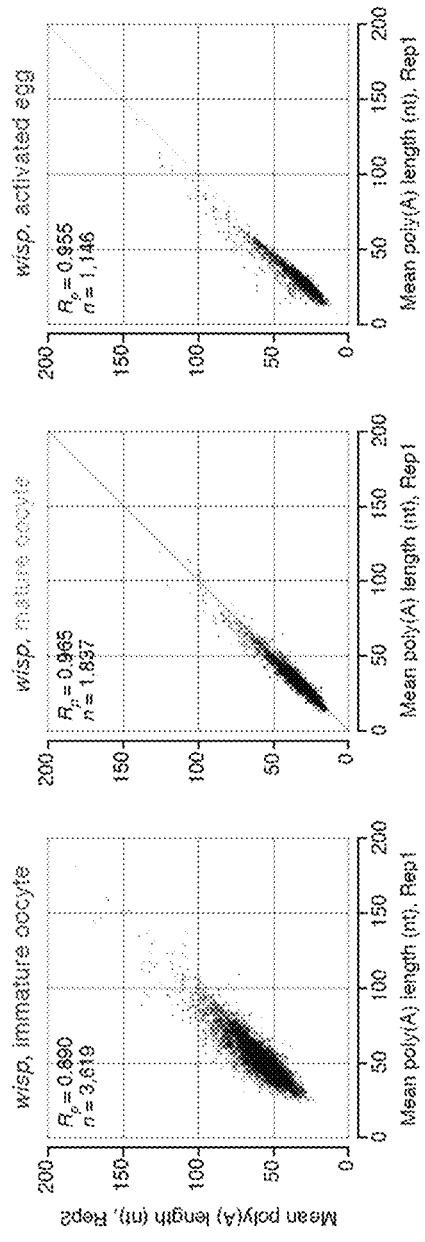
FIGS. 7a-7c illustrate changes of poly(A) tail length and mRNA abundance in wisp mutants.

To verify the global cytoplasmic polyadenylation that we observed in late oogenesis, we carried out mTAIL-seq on wisp mutants (FIG. 7a). Wispy is a noncanonical poly(A) polymerase that is expressed exclusively in maturing oocytes and early embryos (Benoit et al. 2008; Cui et al. 2008; Lee et al. 2014), Wispy acts on mRNAs and microRNAs (miRNAs). The specificity of Wispy on individual transcripts was addressed previously with a microarray approach (Cui et al. 2013) but needs to be investigated with higher resolution. In immature oocytes, poly(A) tail lengths in wisp mutants were similar to those in wild type (median of mean length: 56 nt vs. 58 nt), indicating that the activity of Wispy may be limited until this stage (FIG. 8a, left panel).

Figure 7B:
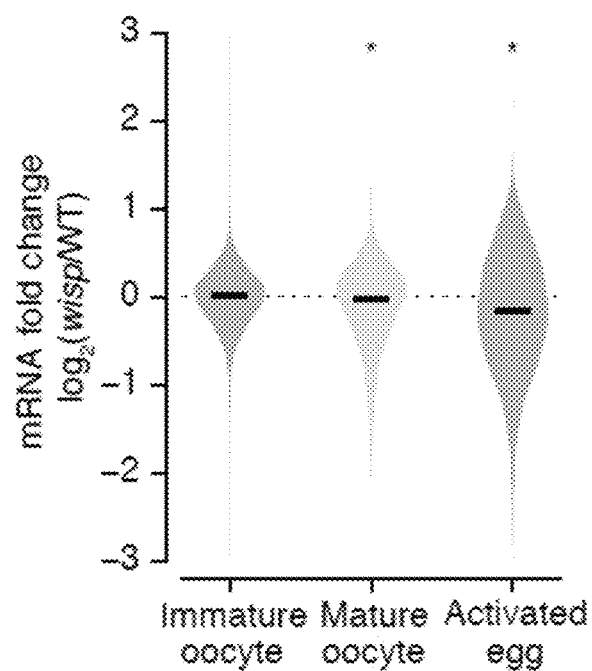
Figure 8A:
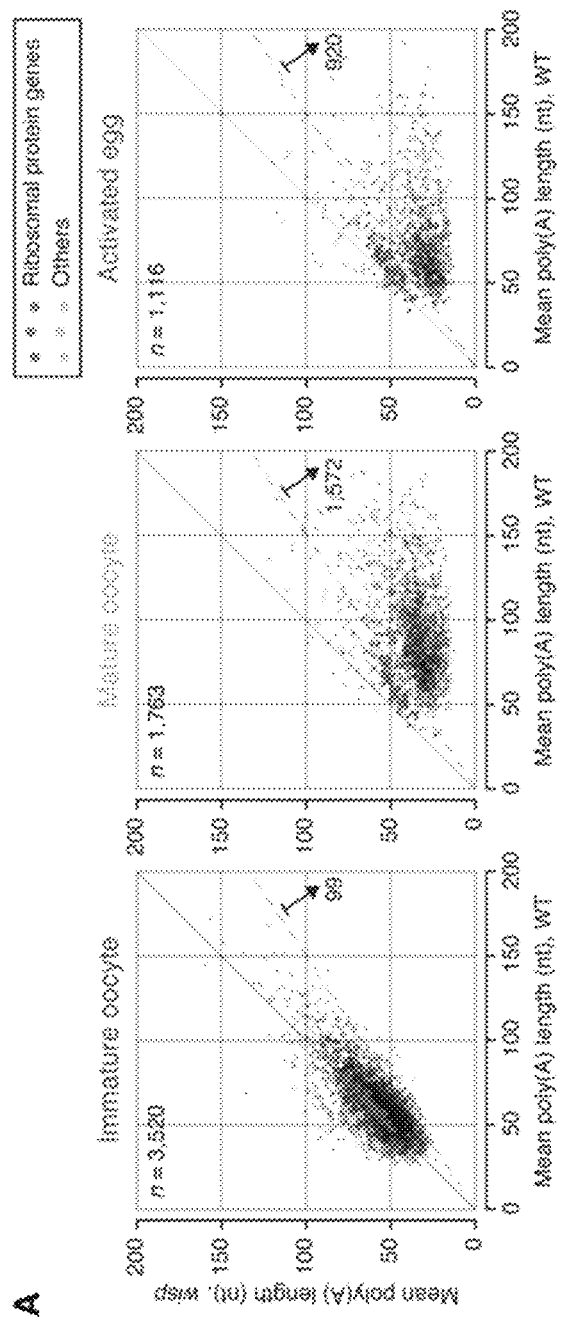
FIGS. 8a-8c illustrate defects of cytoplasmic polyadenylation in wisp mutants.

In stark contrast, mature oocytes displayed a marked difference between wild type and wisp mutants (FIG. 8a, middle panel). The mutant had substantially shorter poly(A) tails than the wild type (median of mean length: 34 nt and 76 nt, respectively). We also observed a comparable difference in activated eggs (median of mean length: 32 nt and 70 nt in the mutant and wild type, respectively) (FIG. 8a, right panel). Gene-level analyses revealed that most mRNA species have shorter poly(A) tails in wisp mutants (98.9% and 97.8% of detected genes in mature oocytes and activated eggs, respectively). Moreover, when examining those genes that displayed changes in poly(A) length by >1.5-fold (FIG. 8a, indicated by dashed lines), 89.2% and 82.4% of genes carried shorter poly(A) tails in mutant mature oocytes and activated eggs, respectively. Thus, Wispy is responsible for most, if not all, polyadenylation events at these developmental stages. This observation is consistent with the above results (FIG. 4) showing that cytoplasmic polyadenylation takes place mainly during late oogenesis, although Wispy may act either before stage 9 or after egg activation on some select transcripts. We also noticed that mRNA abundance is modestly reduced in activated eggs of wisp mutants as compared with those of the wild type (FIG. 7b), suggesting that Wispy may increase the stability of maternal mRNAs during embryogenesis.

Figure 8B:
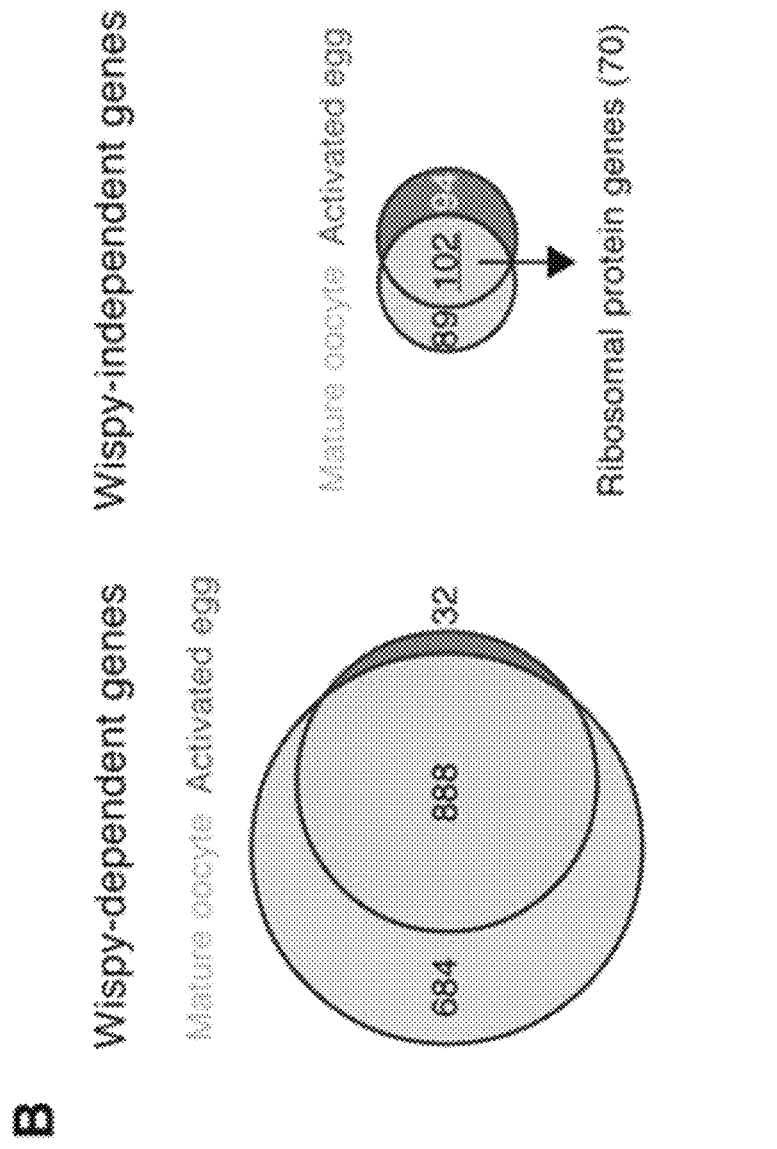

This data allowed us to identify a group of genes that are refractory to Wispy (FIG. 7a, shown by red dots). This group includes 191 genes (10.8%) and 196 genes (17.6%) detected in mature oocytes and activated eggs, respectively (FIG. 8b). Notably, most of them encode ribosomal proteins (FIG. 8b). Consistently, these mRNA species belong to "group 8," whose poly(A) tails do not change in length in wild type during both late oogenesis and egg activation (FIG. 5). These data suggest that the transcripts encoding ribosomal proteins may specifically escape from cytoplasmic polyadenylation.

Figure 7C:
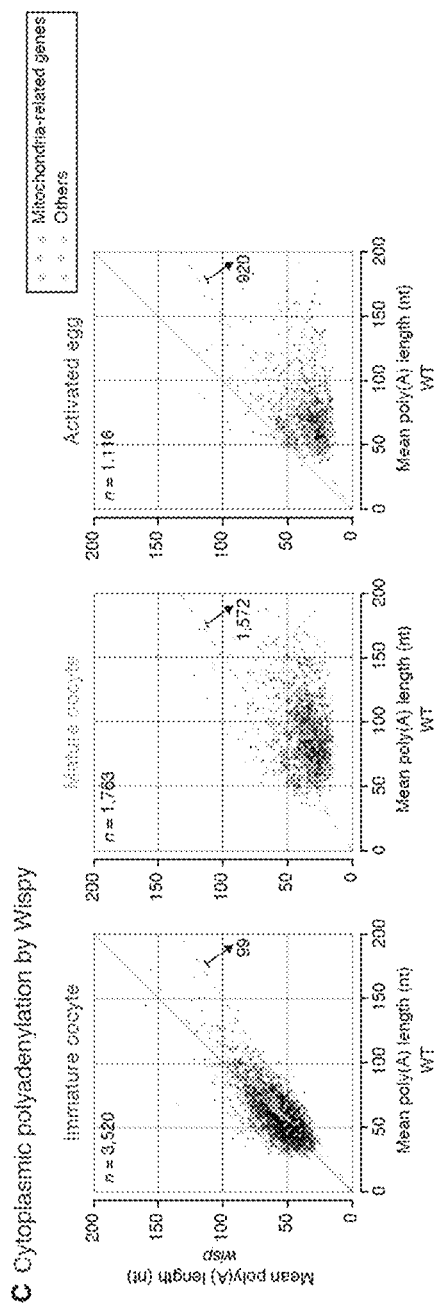

Of note, it was previously reported that genes involved in mitochondrial function are independent of Wispy (Cui et al. 2013): however, we found that such genes displayed changes in poly(A) tail length in a Wispy-dependent manner (Supplemental FIG. 7c, shown as green dots). The apparent discrepancy between the studies is likely because the previous approach relied on an oligo(dT) column. The column captures mRNAs with long A tails (more than 40 nt) indiscriminately (Cui et al. 2013).

Figure 8C:
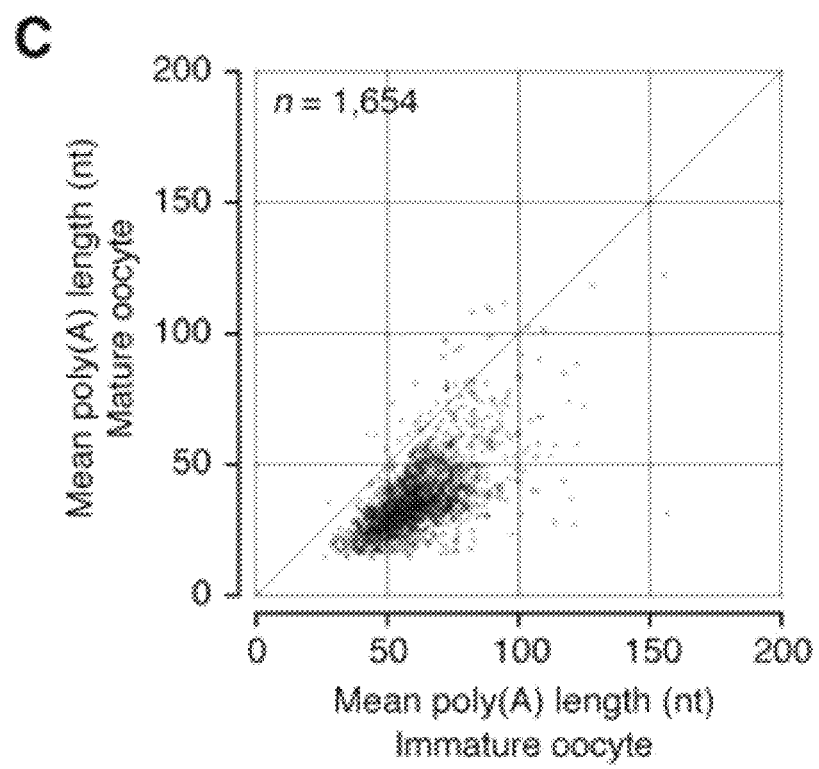

Our analysis also revealed that, in the absence of Wispy, poly(A) length continues to decrease instead of staying the same (FIG. 8c). The median length changed from 56 nt (at stage 9-10) to 34 nt (at stage 14) (FIG. 8c). This result implies that Wispy may be required for not only polyadenylation but also protection against deadenylation during late oogenesis.

Correlation Between Poly(A) Tail Length and Translational Efficiency (TE)

To understand the functional consequences of cytoplasmic polyadenylation, we compared poly(A) tail length with TE. It was shown recently that poly(A) length correlates with TE in zebrafish and frog embryos before zygotic transcription, while there is no such correlation in somatic cells (Subtelny et al. 2014). It remains unknown whether invertebrate embryos have comparable regulatory mechanism at the genomic scale.

Figure 9A:
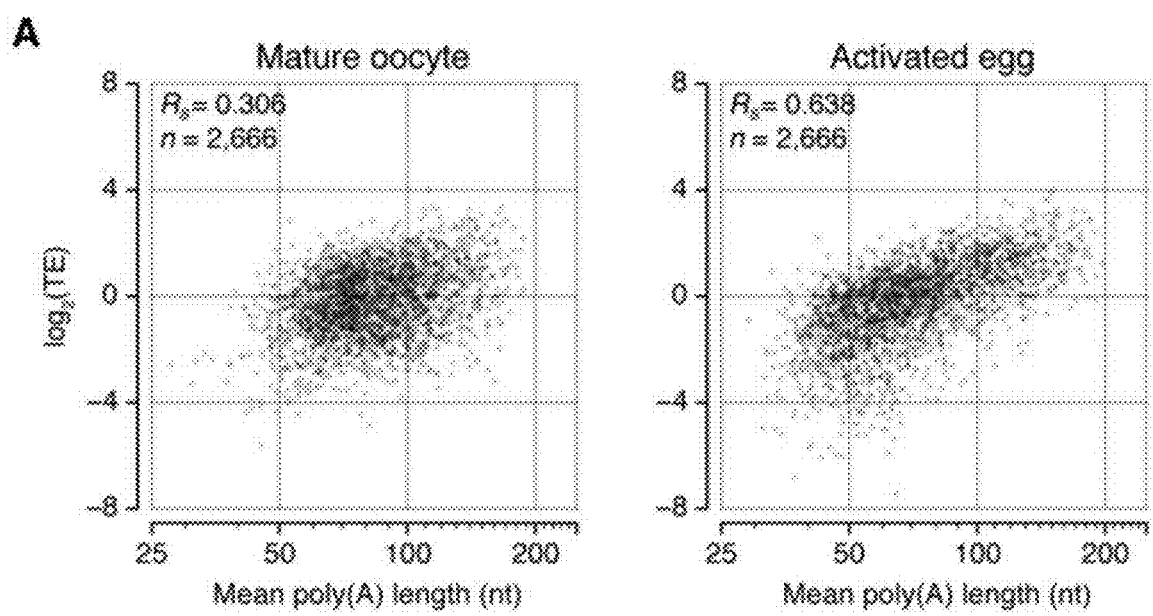
FIGS. 9a-9c illustrate functional association of poly(A) tail length and translation during egg activation.
Figure 10A:
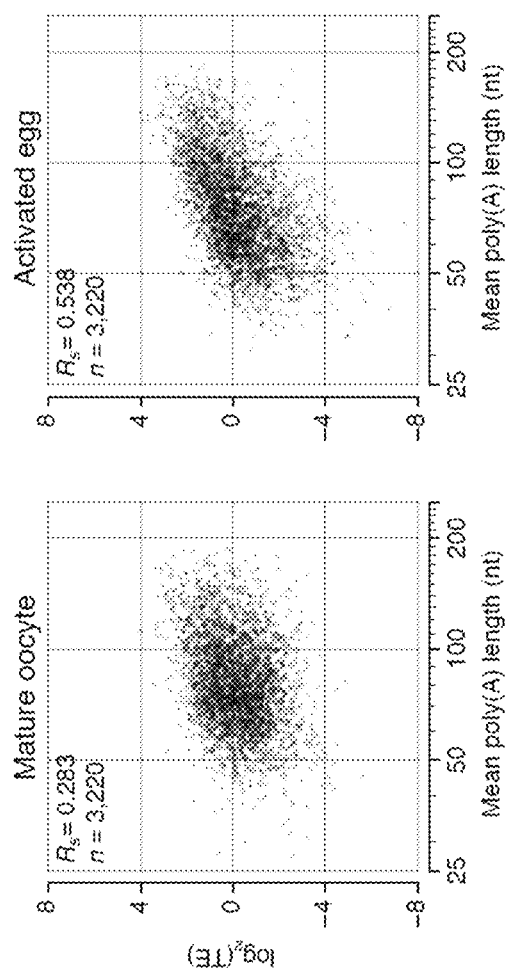
FIGS. 10a-10c illustrate correlation between poly(A) tail length and translation.

Orr-Weaver and colleagues (Kronja et al. 2014) previously measured TE by ribosome profiling in mature oocytes and activated eggs (0-2 h). To match the developmental stage, we generated a poly(A) tail profile of the 0- to 2-h activated eggs in addition to the 0- to 1-h activated eggs (FIG. 9a; FIG. 10a). The comparison of the poly (A) profile and ribosome profile showed a clear correlation between poly(A) tail length and TE in activated eggs (Rs=0.638) (FIG. 9a, right panel). Thus, like in vertebrates, protein synthesis is mainly and globally dictated by the poly (A) tail in early embryos of Drosophila. This result confirms earlier studies on individual genes (Benoit et al. 2008; Coll et al. 2010) and further suggests that animals have a highly conserved mechanism for the regulation of the earliest translation events.

Figure 9B:
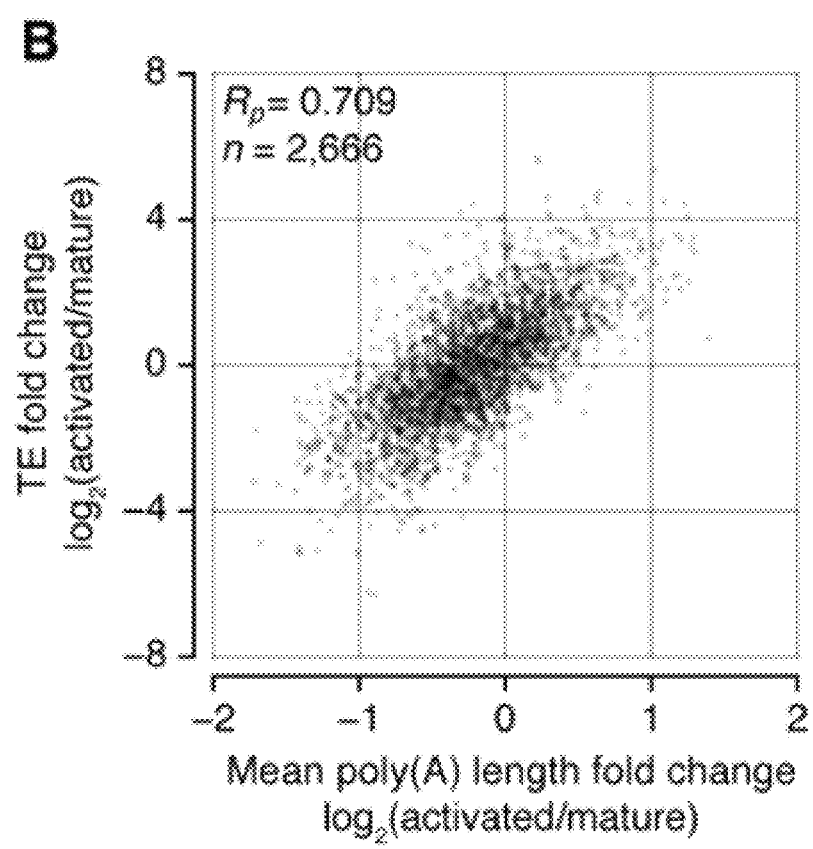
Figure 10B:
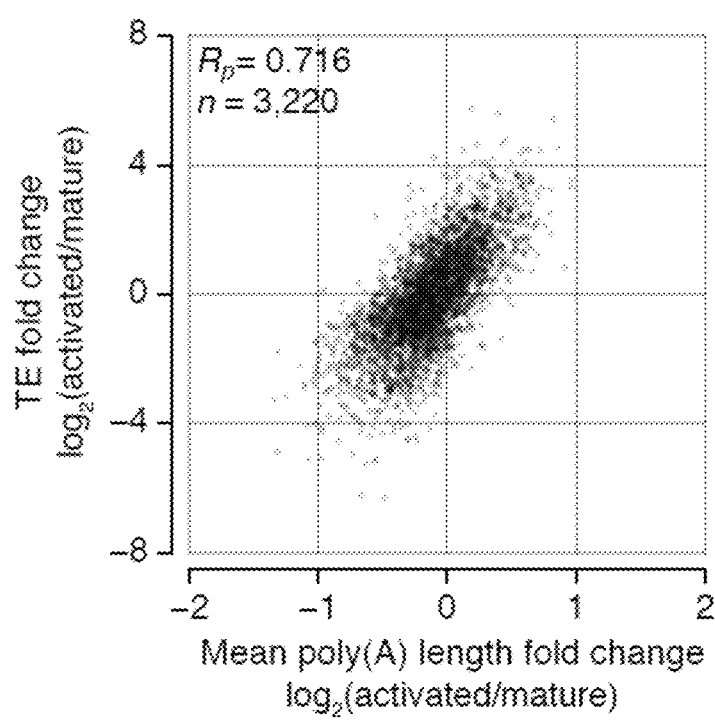
Figure 10C:
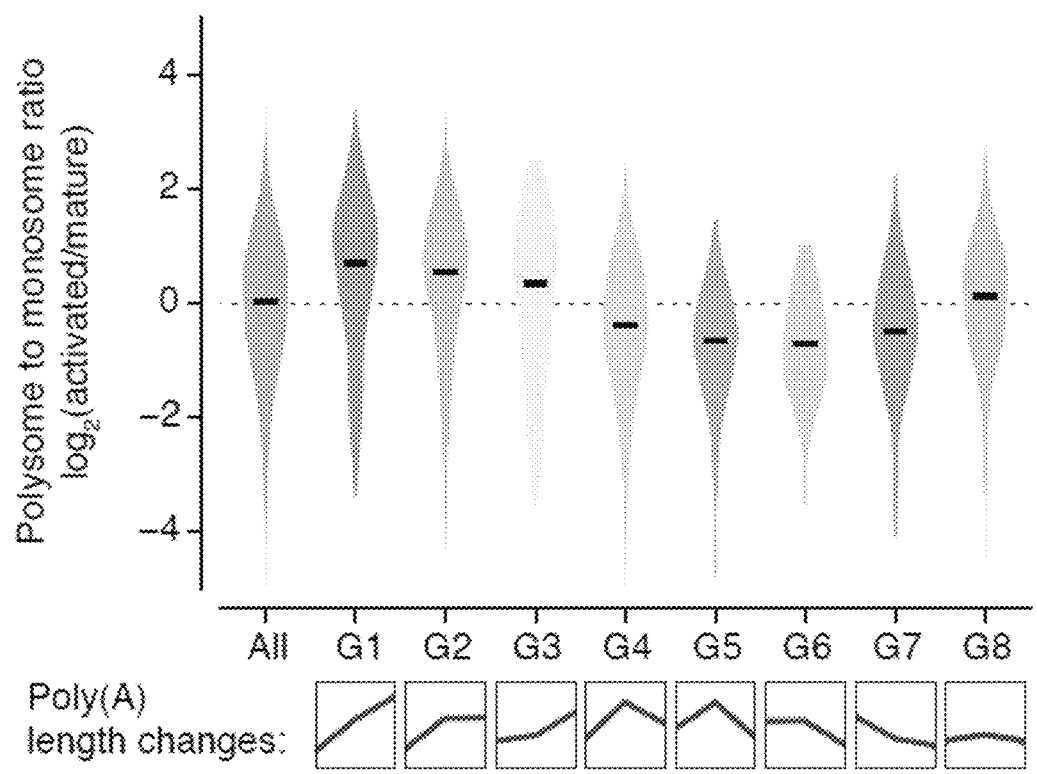

A notable observation from this analysis is that the correlation is modest in mature oocytes (Rs=0.306) (FIG. 9a, left panel). This was unexpected because the global poly (A) distribution does not change substantially during egg activation (FIG. 4b). Nevertheless, it is noteworthy that many individual genes are modulated in poly(A) tails during egg activation (FIG. 4c, right). The changes in poly(A) tail length during egg activation correlate well to the changes in TE (FIG. 9b; FIG. 10b). These results suggest that while global elongation occurs during late oogenesis, the additional modulation of poly(A) tail length during egg activation may be important for translational control. The polysome/monosome ratio in activated eggs is fivefold higher than that in mature oocytes, indicating that translation is globally up-regulated during egg activation (Kronja et al. 2014). Thus, in flies, polyadenylation and translational activation appear to be partly separated. Polyadenylation begins during late oogenesis, while translational activation occurs later during egg activation.

Figure 9C:
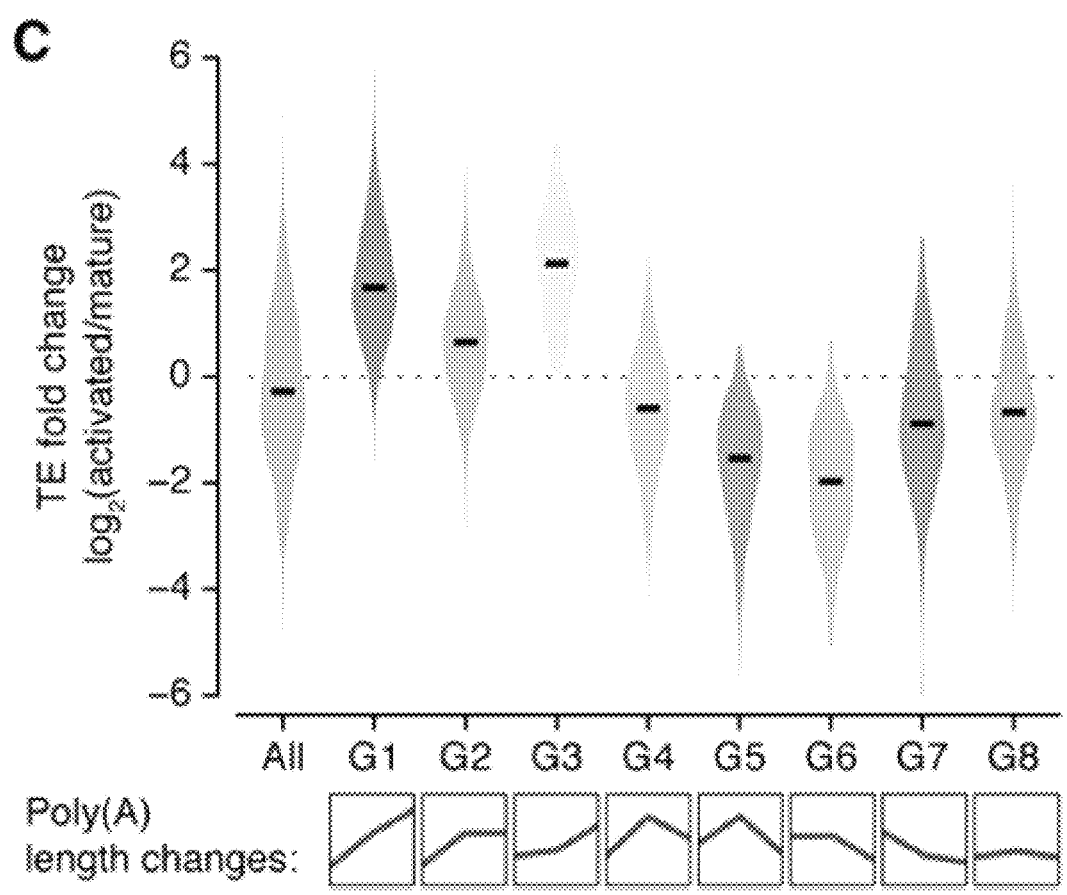

We next compared TEs of different groups of transcripts that show distinct patterns of poly(A) tail length (FIGS. 5a, 9c). Transcripts in groups 1, 2, and 3 whose poly(A) tails are continuously elongated showed a dramatic increase of TE upon egg activation (FIG. 9c). In contrast, genes in groups 5 and 6, which include many energy metabolism related genes, are translationally suppressed. Poly(A) tails continue to be modified during egg activation, presumably by concurrent polyadenylation and deadenylation. For instance, transcripts encoding the vacuolar H+ATPase subunit and cytochrome C oxidase subunit are deadenylated and translationally suppressed during egg activation. Transcripts in group 8 [those with little changes in poly(A) tails] tend to be translated at constant rates. We obtained similar results when we applied another index for translation rate, the ribosome occupancy, which is the ratio of RNA associated with polysomes over monosomes. Taken together, our analyses demonstrate that the regulation of the poly(A) tail shapes the translational landscape in early embryos.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

The invention claimed is:

1. A 3' hairpin adaptor for analyzing the 3' end sequences of messenger RNA (mRNA), the 3' hairpin adaptor comprising, in a 5' to 3' direction:
   i) a first stem region including 6-12 base pairs, wherein the base pairs are base pairs including nucleotides of a 5' arm, self-hybridized with nucleotides of a 3' arm;
   ii) a first loop region including a 5' arm including 10-20 unpaired nucleotides, wherein a 3' arm corresponding to the 5' arm includes nucleotides unpaired with the 5' arm or is a spacer;
   iii) a second stem region including 10-22 base pairs, wherein the base pairs are base pairs including nucleotides of a 5' arm, self-hybridized with nucleotides of a 3' arm, and include at least one biotinylated nucleotide at a 5' end of the 3' arm, hybridized with a 3' end of the 5' arm, in the stem region;
   iv) a second loop region including an endonuclease recognition site, wherein the second loop region is configured to form a loop end; and
   v) a poly(A) tail binding region linked to the 3' arm of the first stem region in an overhang manner.

2. The 3' hairpin adaptor of claim 1, wherein a 5' end of the 5' arm of the first stem region is phosphorylated.

3. The 3' hairpin adaptor of claim 1, wherein a 3' end of the 3' arm of the first stem region further includes 3' inverted deoxythymidine (3InvdT).

4. The 3' hairpin adaptor of claim 1, wherein the biotinylated nucleotide iii) is a biotinylated thymine.

5. The 3' hairpin adaptor of claim 1, wherein the endonuclease is apurinic/apyrimidinic endonuclease 1 (APE1) and a recognition site of the endonuclease is internal 1',2'-dideoxyribose (idSP).

6. The 3' hairpin adaptor of claim 1, wherein the second loop region iv) includes a C3 spacer.

7. The 3' hairpin adaptor of claim 1, wherein the poly(A) tail binding site includes 6-12 thymine nucleotides.

8. The 3' hairpin adaptor of claim 1, wherein the poly(A) tail binding site comprises a nucleotide sequence of 5'-TTTTTTTT-3' 5'-ATTTTTTT-3' or 5-AATTTTTT-3'.

9. The 3' hairpin adaptor of claim 1, wherein the 3' hairpin adaptor comprises a structure of (SEQ ID NO: 20)
5'-/5Phos/CTGACATGNNNNNNNNNNNNNTGGAATTCTCGGGTGCCAAGGC/iSpC3//idSp//idSp//iBiodT//iBiodT/GGCACCCGAGAATT/iSp18/CATGTCAGTTTTTTTT/3InvdT/-3'.

10. The 3' hairpin adaptor of claim 1, wherein the 3' hairpin adaptor comprises a structure of (SEQ ID NO: 21)
5'-/5Phos/CTGACATGNNNNNNNNNNNNNTGGAATTCTCGGGTGCCAAGGC/iSpC3//idSp//idSp//iBiodT//iBiodT/GGCACCCGAGAATT/iSp18/CATGTCAGATTTTTTT/3InvdT/-3'.

11. The 3' hairpin adaptor of claim 1, wherein the 3' hairpin adaptor comprises a structure of (SEQ ID NO: 22)
5'-/5Phos/CTGACATGNNNNNNNNNNNNNTGGAATTCTCGGGTGCCAAGGC/iSpC3//idSp//idSp//iBiodT//iBiodT/GGCACCCGAGAATT/iSp18/CATGTCAGAATTTTTT/3InvdT/-3'.

* * * * *